US008513185B2

(12) United States Patent
Sigalov

(10) Patent No.: US 8,513,185 B2
(45) Date of Patent: Aug. 20, 2013

(54) INHIBITION OF TREM RECEPTOR SIGNALING WITH PEPTIDE VARIANTS

(76) Inventor: Alexander B. Sigalov, Worcester, MA (US)

( * ) Notice: Subject to any disclaimer, the term of this patent is extended or adjusted under 35 U.S.C. 154(b) by 0 days.

(21) Appl. No.: 13/501,992

(22) PCT Filed: Oct. 13, 2010

(86) PCT No.: PCT/US2010/052566

§ 371 (c)(1), (2), (4) Date: Apr. 13, 2012

(87) PCT Pub. No.: WO2011/047097

PCT Pub. Date: Apr. 21, 2011

(65) Prior Publication Data

US 2012/0202733 A1    Aug. 9, 2012

Related U.S. Application Data

(60) Provisional application No. 61/251,283, filed on Oct. 13, 2009.

(51) Int. Cl.
| | |
|---|---|
| A61K 38/08 | (2006.01) |
| A61P 29/00 | (2006.01) |
| A61P 35/00 | (2006.01) |
| A61P 1/00 | (2006.01) |
| A61P 9/10 | (2006.01) |
| C07K 7/06 | (2006.01) |
| C07K 7/08 | (2006.01) |

(52) U.S. Cl.
CPC .................................... *A61K 38/08* (2013.01)
USPC ............ 514/1.4; 530/322; 530/317; 530/328; 530/326; 530/327; 530/324; 514/21.6; 514/19.3; 514/15.1; 514/16.6; 514/18.6; 514/21.4; 514/21.3; 514/21.1

(58) Field of Classification Search
None
See application file for complete search history.

(56) References Cited

U.S. PATENT DOCUMENTS

| | | | |
|---|---|---|---|
| 6,420,526 B1 | 7/2002 | Ruben | |
| 2002/0128444 A1* | 9/2002 | Gingras et al. | 530/350 |
| 2003/0165875 A1* | 9/2003 | Colonna et al. | 435/6 |
| 2006/0246082 A1 | 11/2006 | Faure et al. | |
| 2008/0193375 A1 | 8/2008 | Chang et al. | |
| 2008/0247955 A1 | 10/2008 | Chatterjee-Kishore et al. | |
| 2009/0012025 A1 | 1/2009 | Hotchkiss et al. | |
| 2009/0075899 A1 | 3/2009 | Sigalov | |
| 2009/0081199 A1 | 3/2009 | Colonna et al. | |

OTHER PUBLICATIONS

Amon, M.A., et al., Lipidation and glycosylation of a T cell antigen receptor (TCR) transmembrane hydrophobic peptide dramatically enhances in vitro and in vivo function. Biochim Biophys Acta, 2006. 1763(8): p. 879-88.
Arenberg, D.A., et al., Inhibition of interleukin-8 reduces tumorigenesis of human non-small cell lung cancer in SCID mice. J Clin Invest, 1996. 97(12): p. 2792-802.
Arenberg, D.A., et al., Interferon-gamma-inducible protein 10 (IP-10) is an angiostatic factor that inhibits human non-small cell lung cancer (NSCLC) tumorigenesis and spontaneous metastases. J Exp Med, 1996. 184(3): p. 981-92.
Arenberg, D.A., et al., Epithelial-neutrophil activating peptide (ENA-78) is an important angiogenic factor in non-small cell lung cancer. J Clin Invest, 1998. 102(3): p. 465-72.
Bouchon, A., J. Dietrich, and M. Colonna, Cutting edge: inflammatory responses can be triggered by TREM-1, a novel receptor expressed on neutrophils and monocytes. J Immunol, 2000. 164(10): p. 4991-5.
Bouchon, A., et al., TREM-1 amplifies inflammation and is a crucial mediator of septic shock. Nature, 2001. 410(6832): p. 1103-7.
Deisseroth, e.a., Use of Blood and Blood Products, in Cancer: Principles and Practice of Oncology, D.V.T.J.e.a. Editors, Editor. 1989, J.B. Lippincott Company: Philadelphia. p. 2045-59.
Dietrich, J., et al., Cutting edge: signal-regulatory protein beta 1 is a DAP12-associated activating receptor expressed in myeloid cells. J Immunol, 2000. 164(1): p. 9-12.
Ford, J.W. and D.W. McVicar, TREM and TREM-like receptors in inflammation and disease. Curr Opin Immunol, 2009. 21(1): p. 38-46.
Gerber, D., N. Sal-Man, and Y. Shai, Two motifs within a transmembrane domain, one for homodimerization and the other for heterodimerization. J Biol Chem, 2004. 279(20): p. 21177-82.
Gibot, S., et al., A soluble form of the triggering receptor expressed on myeloid cells-1 modulates the inflammatory response in murine sepsis. J Exp Med, 2004. 200(11): p. 1419-26.
Gibot, S., Clinical review: role of triggering receptor expressed on myeloid cells-1 during sepsis. Crit Care, 2005. 9(5): p. 485-9.
Gibot, S., et al., Effects of the TREM 1 pathway modulation during hemorrhagic shock in rats. Shock, 2009. 32(6): p. 633-7.
Gibot, S., et al., Effects of the TREM-1 pathway modulation during mesenteric ischemia-reperfusion in rats. Crit Care Med, 2008. 36(2): p. 504-10.
Harbury, P.B., et al., High-resolution protein design with backbone freedom. Science, 1998. 282(5393): p. 1462-7.

(Continued)

*Primary Examiner* — Karlheinz R Skowronek
*Assistant Examiner* — Mindy Newman
(74) *Attorney, Agent, or Firm* — SciTech Legal, P.C.; Yakov M. Korkhin, Esq.

(57) ABSTRACT

Peptides are provided consisting of L- and/or D-amino acids and combinations thereof, which affect myeloid cells by action on the triggering receptors expressed on myeloid cells (TREMs), including TREM-1 and TREM-2. The peptides act on the TREM/DAP-12 signaling complex. Also provided are lipid and sugar conjugated peptides comprising L- or D-amino acids. A method is provided of designing the peptides and lipid- and/or sugar-conjugated peptides comprising L- or D-amino acids. The disclosure relates to the therapy of various myeloid cell-related disease states involving the use of these peptides and compounds. The peptides and compounds are useful in the treatment and/or prevention of a disease or condition where myeloid cells are involved or recruited. The peptides of the present invention also are useful in the production of medical devices comprising peptide matrices (for example, medical implants and implantable devices).

28 Claims, 11 Drawing Sheets

(56) References Cited

OTHER PUBLICATIONS

Ho, C.C., et al., TREM-1 expression in tumor-associated macrophages and clinical outcome in lung cancer. Am J Respir Crit Care Med, 2008. 177(7): p. 763-70.

Keegan, A.D. and W.E. Paul, Multichain immune recognition receptors: similarities in structure and signaling pathways. Immunol Today, 1992. 13(2): p. 63-8.

Klesney-Tait, J., I.R. Turnbull, and M. Colonna, The TREM receptor family and signal integration. Nat Immunol, 2006. 7(12): p. 1266-73.

Kliger, Y., et al., Fusion peptides derived from the HIV type 1 glycoprotein 41 associate within phospholipid membranes and inhibit cell-cell Fusion. Structure-function study. J Biol Chem, 1997. 272(21): p. 13496-505.

Koch, A.E., P.J. Polverini, and S.J. Leibovich, Stimulation of neovascularization by human rheumatoid synovial tissue macrophages. Arthritis Rheum, 1986. 29(4): p. 471-9.

Lock, G., Acute intestinal ischaemia. Best Pract Res Clin Gastroenterol, 2001. 15(1): p. 83-98.

Luo, L., et al., Effects of the TREM-1 pathway modulation during empyema in rats. Chin Med J (Engl), 2010. 123(12): p. 1561-5.

Merrifield, R.B., L.D. Vizioli, and H.G. Boman, Synthesis of the antibacterial peptide cecropin A (1-33). Biochemistry, 1982. 21(20): p. 5020-31.

Murakami, Y., et al., Intervention of an inflammation amplifier, triggering receptor expressed on myeloid cells 1, for treatment of autoimmune arthritis. Arthritis Rheum, 2009. 60(6): p. 1615-23.

Nakajima, H., et al., Human myeloid cells express an activating ILT receptor (ILT1) that associates with Fc receptor gamma-chain. J Immunol, 1999. 162(1): p. 5-8.

Phillips, R.J., et al., The stromal derived factor-1/CXCL12-CXC chemokine receptor 4 biological axis in non-small cell lung cancer metastases. Am J Respir Crit Care Med, 2003. 167(12): p. 1676-86.

Piccio, L., et al., Blockade of TREM-2 exacerbates experimental autoimmune encephalomyelitis. Eur J Immunol, 2007. 37(5): p. 1290-301.

Schenk, M., et al., TREM-1—expressing intestinal macrophages crucially amplify chronic inflammation in experimental colitis and inflammatory bowel diseases. J Clin Invest, 2007. 117(10): p. 3097-106.

Sharif, O. and S. Knapp, From expression to signaling: roles of TREM-1 and TREM-2 in innate immunity and bacterial infection. Immunobiology, 2008. 213(9-10): p. 701-13.

Sigalov, A.B., Multichain immune recognition receptor signaling: different players, same game? Trends Immunol, 2004. 25(11): p. 583-9.

Sigalov, A., Multi-chain immune recognition receptors: spatial organization and signal transduction. Semin. Immunol., 2005. 17(1): p. 51-64.

Sigalov, A.B., Immune cell signaling: a novel mechanistic model reveals new therapeutic targets. Trends Pharmacol Sci, 2006. 27(10): p. 518-24.

Sigalov, A.B., Transmembrane interactions as immunotherapeutic targets: lessons from viral pathogenesis. Adv Exp Med Biol, 2007. 601: p. 335-44.

Sigalov, A.B., Signaling chain homooligomerization (SCHOOL) model, in Multichain Immune Recognition Receptor Signaling: From Spatiotemporal Organization to Human Disease, A.B. Sigalov, Editor. 2008, Springer-Verlag New York Inc: New York. p. 121-163.

Sigalov, A.B., SCHOOL model and new targeting strategies, in Multichain Immune Recognition Receptor Signaling: From Spatiotemporal Organization to Human Disease, A.B. Sigalov, Editor. 2008, Springer-Verlag New York Inc: New York. p. 268-311.

Weidner, N., Intratumor microvessel density as a prognostic factor in cancer. Am J Pathol, 1995. 147(1): p. 9-19.

Whittaker, R.G., P.J. Hayes, and V.J. Bender, A gentle method for linking Tris to amino acids and peptides. Pept Res, 1993. 6(3): p. 125-8.

Yamashita, Y., M. Ono, and T. Takai, Inhibitory and stimulatory functions of paired Ig-like receptor (PIR) family in RBL-2H3 cells. J Immunol, 1998. 161(8): p. 4042-7.

Yang, R., et al., Ethyl pyruvate ameliorates distant organ injury in a murine model of acute necrotizing pancreatitis. Crit Care Med, 2004. 32(7): p. 1453-9.

\* cited by examiner

A proposed mode of action of TREM-1 core peptide

TREM-1

TREM-1 TRANSMEMBRANE PEPTIDES

Core:
GFLSKSLVF

Extended:
LLAGGFLSKSLVFSVL

DAP12 subunit dimer

CORE/EXTENDED PEPTIDE

TREM-1

MODULATION OF BINDING

CORE PEPTIDE:

F9K/R (Phe9 -> Lys/Arg)

G1K/R F9/K/R) (Gly1 and Phe9 -> Lys/Arg)

L7K/R (Leu7 ->Lys/Arg)

EXTENDED PEPTIDE:

L11K/R (Leu11 ->Lys/Arg)

INHIBITION OF TREM RECEPTOR SIGNALING WITH PEPTIDE VARIANTS

CROSS-REFERENCE TO RELATED APPLICATIONS

This application is a National Stage entry of International Application No. PCT/US10/52566, filed on Oct. 13, 2010, which claims priority to and the benefit of U.S. provisional application Ser. No. 61/251,283, filed Oct. 13, 2009. The entire content of the aforementioned applications is incorporated herein by reference.

FIELD OF THE INVENTION

The present invention relates to peptides and compounds which affect the activating TREM receptor signaling pathway in granulocytes, monocytes, macrophages, neutrophils, microglia, dendritic cells, osteoclasts, platelets and other myeloid cells. The present invention further relates to the treatment or prevention of cancer, allergic diseases, inflammatory bowel disease, empyema, acute mesenteric ischemia, hemorrhagic shock, autoimmune diseases, including but not limited to, rheumatoid arthritis and other rheumatic diseases, sepsis and other inflammatory or other condition involving myeloid cell activation, and, more particularly, TREM receptor-mediated cell activation. In one embodiment, TREM-1/DAP-12 receptor complex signaling is inhibited by variant peptides binding to the transmembrane region of the DAP-12 subunit.

BACKGROUND OF THE INVENTION

1. TREM Receptors

Innate immunity is crucial for host survival during the early stages of infection. However, fine-tuning of this response is absolutely crucial to prevent excessive inflammation and tissue damage (Ford J. W. & McVicar D. W. Curr Opin Immunol 2009; 21, 38-46). Pathogen sensing is achieved through a constellation of pathogen recognition receptors, such as the toll-like receptors (TLR), which activate innate immune cells to clear the pathogen and to shape the adaptive immune response. Other innate immune receptors, such as the triggering receptor expressed on myeloid cells (TREM), modulate the innate response either by amplifying or dampening TLR-induced signals, and thus play crucial roles in fine-tuning of the inflammatory response. Since the discovery of triggering receptor expressed on myeloid cells (TREM)-1 in 2000, evidence documenting the profound ability of the TREM and TREM-like receptors to regulate inflammation has rapidly accumulated (Bouchon et al. J Immunol 2000; 164:4991-5; Ford J. W. & McVicar D. W. Curr Opin Immunol 2009; 21, 38-46; Bouchon et al. Nature 2001; 410:1103-7; Gibot S. Crit Care 2005; 9:485-9; Gibot et al. J Exp Med 2004; 200:1419-26; Gibot et al. Shock 2009; 32:633-7; Gibot et al. Crit Care Med 2008; 36:504-10; Klesney-Tait et al. Nat Immunol 2006; 7:1266-73; Murakami et al. Arthritis Rheum 2009; 60:1615-23; Sharif O. & Knapp S. Immunobiology 2008; 213:701-13; Ling et al. Chinese Med J 2010; 123:1561-5). The TREM and TREM-like receptors are a structurally related protein family encoded by genes clustered on mouse chromosome 17C3 and human chromosome 6p21. The TREM cluster includes genes encoding TREM-1, TREM-2 and, in the mouse, TREM-3, as well as the 'TREM-like' genes. The 'TREM-like' genes Treml1 and Treml2 in mouse, and TREML1 and TREML2 in humans, encode TREM-like transcripts 1 and 2 (TLT-1 and TLT-2, respectively). Monocytes, macrophages, myeloid dendritic cells, plasmacytoid dendritic cells, neutrophils, microglia, osteoclasts, and platelets all express at least one member of the TREM family, underscoring the importance of these proteins in the regulation of innate resistance, are expressed on a variety of innate cells of the myeloid lineage including neutrophils, monocytes, macrophages, microglia, osteoclasts, and dendritic cells, as well as on megakaryocytes and platelets.

Recent work on the TREM family includes: characterization of a new receptor expressed on plasmacytoid dendritic cells; definition of a key role for TREM in sepsis, cancer, inflammatory bowel disease and multiple sclerosis; an expanded list of diseases associated with the release of soluble forms of TREM proteins; and identification of the first well characterized TREM ligand: B7-H3, a ligand for TLT-2. Moreover, analysis of TREM signaling has now identified key regulatory components and defined pathways that may be responsible for the complex functional interactions between the TREM and TLRs. Together these findings define the TREM receptors as pluripotent modifiers of disease through the integration of inflammatory signals with those associated with leukocyte adhesion.

2. TREM-Related Pathologies

2.1. Sepsis

Septicemia, an invasion of the bloodstream by virulent bacteria that multiply and discharge their toxic products, is the serious and sometimes fatal disorder, commonly known as blood poisoning. The invasive organisms are usually streptococci or staphylococci but may be any type of bacteria. Septicemia is an extremely dangerous disorder because it spreads rapidly throughout the body. If bacteria continue to multiply in the bloodstream and the condition progresses to septic shock, blood pressure plummets and organ systems begin to shut down. Septic shock is characterized by massive release of proinflammatory mediators and leads not only to tissue damage, but also to haemodynamic changes, multiple organ failure (multiple-organ dysfunction syndrome, MODS), and ultimately death. More than 750,000 cases of sepsis occur annually in the US, and 215,000 of those afflicted die even with intensive medical care that includes antibiotics, intravenous fluids, blood transfusions, kidney dialysis, nutritional and respiratory support and sometimes surgery to remove the source of an infection. The incidence of sepsis has nearly doubled in the last decade and is expected to rise further, as the population ages and more people survive with conditions that leave them vulnerable. Despite the use of potent antibiotics and advanced resuscitative equipment costing $17 billion a year, septic shock remains the most common cause of death in non-coronary intensive care units (ICUs). Despite advances in methods and compositions for treatment of sepsis (US Pat Appl 20090012025), activated protein C (Xigris, drotrecogin-alpha, marketed by Eli Lilly) is the only FDA-approved drug for sepsis. However, Xigris has a very limited use—only in patients with high risk of death. Xigris should only be administered in an ICU and has significantly less effective protection if delayed in practice. Also, its use is limited to non-surgical patients due to the adverse effects on coagulation. Thus, there is a great need for an effective novel treatment for sepsis.

Initial findings established TREM-1 as an amplifier of the systemic inflammatory response syndrome associated with sepsis. Blockade of TREM-1 has been shown to protect mice against lipopolysaccaride (LPS)-induced shock, as well as microbial sepsis caused by live *Escherichia coli* or caecal ligation and puncture (Bouchon et al. Nature 2001; 410, 1103-7). These results demonstrate a critical function of TREM-1 in acute inflammatory responses to bacteria and implicate TREM-1 as a promising therapeutic target for sepsis.

2.2. Acute Mesenteric Ischemia

Acute mesenteric ischemia is an abdominal emergency associated with 60 to 90% mortality (Lock G. Best Pract Res Clin Gastroenterol 2001; 15:83-98; Gibot et al. Crit Care Med 2008; 36:504-10). Although ischemia by itself induces little damage, reperfusion of the previously ischemic organ can yield to remote organ injury and life-threatening multiple organ failure. Even though numerous modalities and substances have been studied to reduce gut ischemia/reperfusion (I/R)-induced mortality, none have been entirely successful. As such, the development of effective strategies for preventing and treating circulatory collapse and organ injury after gut I/R is critical for the improvement of patient outcome under such conditions.

Recently, inhibition of TREM-1 has been shown to prevent an I/R-induced marked increase in ileal mucosal permeability and an associated bacterial translocation and to delay mortality (Gibot et al. Crit Care Med 2008; 36:504-10), indicating that the inhibition of the TREM-1 pathway may be useful during acute mesenteric ischemia.

2.3. Hemorrhagic Shock

Hemorrhagic shock is a condition of reduced tissue perfusion, resulting in the inadequate delivery of oxygen and nutrients that are necessary for cellular function. Whenever cellular oxygen demand outweighs supply, both the cell and the organism are in a state of shock. Hemorrhagic shock is primarily caused by traumatic injury, from automobile accidents, bullet or knife wounds, and falls. Trauma causes approximately 150,000 deaths per year, and is the leading cause of death in the population under age 45 in the United States. The resulting loss of productive life years exceeds that of any other disease, with estimated societal costs of >$450 billion annually. Most trauma deaths result from insufficient tissue perfusion due to excessive blood loss. Clinical management of hemorrhagic shock relies on massive and rapid infusion of fluids to maintain blood pressure. However, the majority of victims with severe blood loss do not respond well to fluid restoration. The development of effective strategies for resuscitation of traumatic blood loss, therefore, is urgently needed.

Recently, it has been shown that early inhibition of the TREM-1 pathway may be useful during severe hemorrhagic shock in rats in preventing organ dysfunction and improving survival (Gibot et al. Shock 2009; 32:633-7).

2.4. Rheumatoid Arthritis and Other Rheumatic Diseases

Rheumatic diseases are characterized by inflammation (signs are redness and/or heat, swelling, and pain) and loss of function of one or more connecting or supporting structures of the body. They especially affect joints, tendons, ligaments, bones, and muscles. Common symptoms are pain, swelling, and stiffness. Some rheumatic diseases can also involve internal organs. There are more than 100 rheumatic diseases including but not limiting to arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, and chronic fatigue syndrome. Rheumatic diseases may cause pain, stiffness, and swelling in the joints and other supporting body structures, such as muscles, tendons, ligaments, and bones. However, rheumatic diseases can affect other areas of the body, including internal organs. Some rheumatic diseases involve connective tissues (called connective tissue diseases), while others may be caused by autoimmune disorders, which are diseases involving the body's immune system attacking its own healthy cells and tissues. Rheumatic diseases are the leading cause of disability among persons age 65 and older. According to the Centers for Disease Control and Prevention, as of 2002, more than 70 million people in the U.S. have some form of arthritis (one in every three adults). This includes roughly 300,000 children that suffer from some form of arthritis or rheumatic disease, and millions more are at risk of developing one of these diseases. Most persons over the age of 75 are affected with osteoarthritis (also called degenerative joint disease) in at least one joint, making this condition a leading cause of disability in the US. Rheumatoid arthritis (RA) is an autoimmune disease characterized by synovial hyperplasia with massive infiltration of inflammatory cells, which leads to degeneration of cartilage, erosion of bone, and ultimately loss of function in the affected joints. Rheumatoid arthritis is the most crippling form of arthritis and affects approximately 2.1 million Americans and two to three times more women than men. Further, the average onset for rheumatoid arthritis is between the ages of 20 and 45 years old. Currently, arthritis disables 19 million Americans and takes a $128 billion toll annually on the U.S. economy in direct and indirect medical costs.

Recently, blockade of TREM-1 has been shown to represent a new promising approach to rheumatic diseases that is safer than the presently available immunosuppressive treatments (Murakami et al. Arthritis Rheum 2009; 60:1615-23).

2.5. Non-Small Cell Lung Cancer

Non-small cell lung cancer (NSCLC) accounts for about 87% of all lung cancer patients and affects more than 1.2 million people a year with around 1.1 million deaths annually in the US and worldwide. Estimated new cases and deaths from lung cancer (non-small cell and small cell combined) in the United States in 2010 are 222,520 and 157,300, respectively. Despite advances made in cytotoxic chemotherapy, NSCLC still kills more patients than breast, colon and prostate cancer taken together. Thus, there is a great need for an effective novel treatment for NSCLC. However, although lung cancer, and particularly primary NSCLC, is the leading cause of malignancy-related mortality in the United States, the biology of this devastating disease is complex and poorly understood.

Recent findings established that TREM-1 and the inflammatory response play an important role in cancer progression. It has been shown that cancer cells can directly up-regulate TREM-1 expression in patients' macrophages and that TREM-1 expression in tumor-associated macrophages is associated with cancer recurrence and poor survival of patients with NSCLC (Ho et al. Am J Respir Crit Care Med 2008; 177:763-70). These results demonstrate a critical function of TREM-1 in cancer progression and implicate TREM-1 as a promising target for the development of new rational anticancer therapy. It can be expected that blocking activation of the TREM-1 pathway may significantly improve survival of patients with NSCLC.

3. Current Approaches to Inhibit the TREM-1 Pathway

Antibodies have been considered as clinically significant therapeutic agents for various TREM-related pathologies (US Pat Appl 20080247955; Piccio et al. Eur J Immunol 2007; 37:1290-301). However, antibody therapy poses serious disadvantages. First, as antibodies are natural products they must be produced in cell lines or other live expression systems. This raises a question that there could be contamination of antibody preparations by infectious agents such as prions or viruses. Although tight regulation and regulatory vigilance and surveillance can reduce this concern, the need for ongoing monitoring and testing for contamination contributes to the high cost of developing and administering antibody therapies. In addition, antibody-based therapies require considerable logistical support. As antibodies are proteins, they cannot be given orally, except for those used to treat certain types of mucosal infectious diseases, and therefore, systemic administration is required. Another serious disadvantage of antibody-based therapies is the high costs of production, storage, and administration. Moreover, long infusions (i.e., for example, an hour or longer) require a hospital environment and are often associated with mild to very severe side effects. For example, in one trial, in which four patients in the U.K. were given an anticancer antibody reactive against an important receptor on T cells (CD28) severe and life-threatening responses were observed; the cause is at present not understood. This makes large-scale clinical applications of a number of monoclonal antibodies with demonstrated therapeutic activity impossible or, at least, severely compromised. Fast degradation of the administered antibodies is another drawback of antibody-based therapy.

As described in US Pat Appls 20090081199 and 20030165875, fusion proteins between human IgG1 constant region and the extracellular domain of mouse TREM-1 or that of human TREM-1 can be used, as a "decoy" receptor, to inhibit TREM-1. However, these large protein molecules have poses serious disadvantages similar to those of antibodies.

U.S. Pat. No. 6,420,526 entitled "186 Secreted Proteins" claims unspecified and unexemplified isolated fragments of TREM-1 containing at least 30 contiguous amino acids of human TREM-1. No biological data relating to such fragments are provided.

Peptides based on TREM-1-derived sequences for disrupting TREM-1 function presumably by blocking binding of the receptor with its cognate ligand have also been disclosed (US Pat Appl 20060246082) or published (Murakami et al. Arthritis Rheum 2009; 60:1615-23; Gibot et al. Crit Care Med 2008; 36:504-10; Gibot et al. Shock 2009; 32:633-7). Despite multiple advantages of these peptides as compared to antibodies, they have relatively low efficacy in terms of inhibiting TREM-1, thus having a high potential for toxicity and side effects. For example, the systemic administration of a synthetic TREM-1 peptide that mimics short highly interspecies-conserved extracellular domains of TREM-1 and is often called as LP-17 suppresses collagen-induced arthritis, although the effect is not as complete as that observed following viral gene transfer (Murakami et al. Arthritis Rheum 2009; 60:1615-23).

What is needed is a broad-based TREM-targeted therapy designed to disrupt protein-protein interactions that may be administered to treat various TREM-related pathologies safely and effectively. It is therefore the object of the present invention to provide therapeutic compounds that can be used to treat various TREM-related disorders.

SUMMARY OF THE INVENTION

The present invention relates to peptides and compounds, which affect myeloid cells by action on the triggering receptors expressed on myeloid cells (TREMs), including TREM-1 and TREM-2. The present invention further relates to the prevention and therapy of various myeloid cell-related disease states involving the use of these peptides and compounds. Specifically, the peptides and compounds are useful in the treatment and/or prevention of a disease or condition where myeloid cells are involved or recruited. The peptides of the present invention also are useful in the production of medical devices comprising peptide matrices (for example, medical implants and implantable devices). In one embodiment, TREM-1 signaling is inhibited by variant TREM-1 peptides binding to the transmembrane region of the DAP-12 subunit.

In one embodiment, the present invention contemplates a variant TREM-1 peptide inhibitor comprising at least one amino acid addition and/or substitution that optimizes binding to a DAP-12 subunit relative to the TREM-1 subunit transmembrane domain (TREM-1 TMD: I-V-I-L-L-A-G-G-F-L-S-K-S-L-V-F-S-V-L-F-A). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprises a disulfide-linked dimer. In one embodiment, the peptide inhibitor includes amino acids selected from the group including, but not limited to, L-amino acids, or D-amino acids.

In another embodiment, the present invention contemplates a method comprising: a) providing; i) a patient having at least one symptom of a medical condition or condition where myeloid cells are involved or recruited; and ii) a variant TREM-1 peptide inhibitor comprising at least one amino acid addition and/or substitution that optimizes binding to a DAP-12 subunit relative to the TREM-1 TMD capable of reducing said TREM-1-mediated cell activation; b) administering said inhibitor to said patient under conditions such that said at least one symptom is reduced. In one embodiment, the medical condition comprises sepsis. In one embodiment, the medical condition comprises non-small cell lung cancer (NSCLC). In one embodiment, the medical condition comprises inflammatory bowel disease. In one embodiment, the medical condition comprises acute mesenteric ischemia. In one embodiment, the medical condition comprises hemorrhagic shock. In one embodiment, the medical condition comprises a rheumatic disease. In one embodiment, the rheumatic disease is selected from the group consisting of arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, and chronic fatigue syndrome.

In one embodiment, the present invention contemplates a peptide inhibitor comprising an amino acid sequence consisting of G-$X_1$-$X_2$-L-S-$X_3$-$X_4$-L-V-$X_5$-$X_6$-$X_7$-$X_8$-$X_9$-$X_{10}$ (SEQ ID NO: 1), wherein $X_1$ consists of G, C or is selected from the group consisting of R, K or H; $X_2$ is selected from the group consisting of L, F or I; $X_3$ is selected from the group consisting of R, K or H; $X_4$ is selected from the group consisting of S or T; $X_5$ consists of F or is selected from the group consisting of R, K or H; $X_6$ consists of S, I, L or nothing; $X_7$ consists of V, I, L, G or nothing; and $X_8$, $X_9$, and $X_{10}$ consist of L, F, A or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprises a disulfide-linked dimer. In one embodiment, the peptide inhibitor includes amino acids selected from the group including, but not limited to, L-amino acids, or D-amino acids.

In another embodiment, the present invention contemplates a method comprising: a) providing; i) a patient having at least one symptom of a medical condition or condition where myeloid cells are involved or recruited; and ii) a peptide inhibitor comprising an amino acid sequence consisting of G-$X_1$-$X_2$-L-S-$X_3$-$X_4$-L-V-$X_5$-$X_6$-$X_7$-$X_8$-$X_9$-$X_{10}$ (SEQ ID NO: 1), wherein $X_1$ consists of G, C or is selected from the group consisting of R, K or H; $X_2$ is selected from the group consisting of L, F or I; $X_3$ is selected from the group consisting of R, K or H; $X_4$ is selected from the group consisting of S or T; $X_5$ consists of F or is selected from the group consisting of R, K or H; $X_6$ consists of S, I, L or nothing; $X_7$ consists of V, I, L, G or nothing; and $X_8$, $X_9$, and $X_{10}$ consist of L, F, A or nothing capable of reducing said TREM-1-mediated cell activation; b) administering said inhibitor to said patient under conditions such that said at least one symptom is reduced. In one embodiment, the medical condition comprises sepsis. In one embodiment, the medical condition comprises NSCLC. In one embodiment, the medical condition comprises inflammatory bowel disease. In one embodiment, the medical condition comprises acute mesenteric ischemia. In one embodiment, the medical condition comprises hemorrhagic shock. In one embodiment, the medical condition comprises a rheumatic disease. In one embodiment, the rheumatic disease is selected from the group consisting of arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, and chronic fatigue syndrome.

In one embodiment, the present invention contemplates a peptide inhibitor comprising an amino acid sequence consisting of $X_1$-$X_2$-$X_3$-G-F-L-S-K-S-L-V-R-V-$X_4$-$X_5$ (SEQ ID NO: 2), wherein $X_1$ consists of G, C or nothing; and $X_2$, $X_3$, $X_4$, and $X_5$ consist of K, R, or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprises a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a medical condition or condition where myeloid cells are involved or recruited; and ii) a peptide inhibitor comprising an amino acid sequence consisting of $X_1$-$X_2$-$X_3$-G-F-L-S-K-S-L-V-R-V-$X_4$-$X_5$ (SEQ ID NO: 2), wherein $X_1$ consists of G, C or nothing; and $X_2$, $X_3$, $X_4$, and $X_5$ consist of K, R, or nothing capable of reducing said TREM-1-mediated cell activation; b) administering said inhibitor to said patient under conditions such that said at least one symptom is reduced. In one embodiment, the medical condition comprises sepsis. In one embodiment, the medical condition comprises NSCLC. In one embodiment, the medical condition comprises inflammatory bowel disease. In one embodiment, the medical condition comprises acute mesenteric ischemia. In one embodiment, the medical condition comprises hemorrhagic shock. In one embodiment, the medical condition comprises a rheumatic disease. In one embodiment, the rheumatic disease is selected from the group consisting of arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, and chronic fatigue syndrome.

In one embodiment, the present invention contemplates a peptide inhibitor comprising an amino acid sequence consisting of $X_1$-$X_2$-$X_3$-L-$X_4$-$X_5$-$X_6$-$X_7$-G-$X_8$-L-S-K-$X_9$-L-V-F-$X_{10}$-$X_{11}$-L-F-$X_{12}$-$X_{13}$-$X_{14}$-$X_{15}$ (SEQ ID NO: 3), wherein $X_1$ consists of G or nothing; and $X_2$, $X_3$, $X_{14}$, and $X_{15}$ consist of K, R, or nothing; $X_4$, $X_5$, $X_6$, and $X_7$ consist of P, A, V, C, L, I, S, G or nothing; $X_8$ consists of F, L or I; $X_9$ consists of S or T; $X_{10}$, $X_{11}$, $X_{12}$, and $X_{13}$ consist of S, I, L, G, V, A, or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprises a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a medical condition or condition where myeloid cells are involved or recruited; and ii) a peptide inhibitor comprising an amino acid sequence consisting of $X_1$-$X_2$-$X_3$-L-$X_4$-$X_5$-$X_6$-$X_7$-G-$X_8$-L-S-K-$X_9$-L-V-F-$X_{10}$-$X_{11}$-L-F-$X_{12}$-$X_{13}$-$X_{14}$-$X_{15}$ (SEQ ID NO: 3), wherein $X_1$ consists of G or nothing; and $X_2$, $X_3$, $X_{14}$, and $X_{15}$ consist of K, R, or nothing; $X_4$, $X_5$, $X_6$, and $X_7$ consist of P, A, V, C, L, I, S, G or nothing; $X_8$ consists of F, L or I; $X_9$ consists of S or T; $X_{10}$, $X_{11}$, $X_{12}$, and $X_{13}$ consist of S, I, L, G, V, A, or nothing capable of reducing said TREM-1-mediated cell activation; b) administering said inhibitor to said patient under conditions such that said at least one symptom is reduced. In one embodiment, the medical condition comprises sepsis. In one embodiment, the medical condition comprises NSCLC. In one embodiment, the medical condition comprises inflammatory bowel disease. In one embodiment, the medical condition comprises acute mesenteric ischemia. In one embodiment, the medical condition comprises hemorrhagic shock. In one embodiment, the medical condition comprises a rheumatic disease. In one embodiment, the rheumatic disease is selected from the group consisting of arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, and chronic fatigue syndrome.

In one embodiment, the present invention contemplates a drug delivery system comprising a variant TREM-1 transmembrane peptide conjugated to a therapeutic drug. In one embodiment, the variant peptide comprises substituted amino acids that optimize hydrophobicity relative to the TREM-1 transmembrane core peptide (Peptide 2, Table 2). In one embodiment, the variant peptide comprises additional amino acids that optimize hydrophobicity relative to the TREM-1 transmembrane core peptide (Peptide 2, Table 2). In one embodiment, the variant peptide comprises additional and substituted amino acids that optimize hydrophobicity relative to the TREM-1 transmembrane core peptide (Peptide 2, Table 2). In one embodiment, the variant peptide comprises substituted amino acids that optimize helicity relative to the TREM-1 transmembrane core peptide (Peptide 2, Table 2). In one embodiment, the variant peptide comprises additional amino acids that optimize helicity relative to the TREM-1 transmembrane core peptide (Peptide 2, Table 2). In one embodiment, the variant peptide comprises additional and substituted amino acids that optimize helicity relative to the TREM-1 transmembrane core peptide (Peptide 2, Table 2). In one embodiment, the helicity comprises inherent helicity. In one embodiment, the helicity comprises induced helicity. In one embodiment, the helicity comprises α-helices. In one embodiment, the therapeutic drug is selected from the group including, but not limited to, anti-cancer drugs, anti-inflammatory drugs, psychotropic drugs, anti-depressant drugs, stimulant drugs, anti-diabetic drugs, cardiovascular drugs, anti-thrombotic drugs, anti-proliferative drugs, or cytotoxic drugs.

In one embodiment, the present invention contemplates a protease-resistance immunotherapeutic peptide comprising a variant TREM-1 transmembrane peptide. In one embodiment, the variant peptide comprises at least one D-amino acid.

In one embodiment, the present invention contemplates a cyclic immunotherapeutic peptide comprising a variant TREM-1 transmembrane peptide.

In one embodiment, the present invention contemplates a disulfide-linked dimer of an immunotherapeutic peptide comprising a variant TREM-1 transmembrane peptide.

In one embodiment, the present invention contemplates a medical device comprising a coating, wherein said coating comprises the peptide derivative of claim 1. In one embodiment, the coating further comprises a polymer. In one embodiment, the polymer is selected from the group including, but not limited to, phosphorylcholine, polyvinyl pyrrolidone, poly(acrylic acid), poly(vinyl acetamide), poly(propylene glycol), poly(ethylene co-vinyl acetate), poly(n-butyl methacrylate) or poly(styrene-b-isobutylene-b-styrene). In one embodiment, the medical device is selected from the group including, but not limited to, stents, grafts, catheters, endoscopes (i.e., for example, laparoscopes), atrial/venous fistulas, or cannulae.

DEFINITIONS

Figure 1:
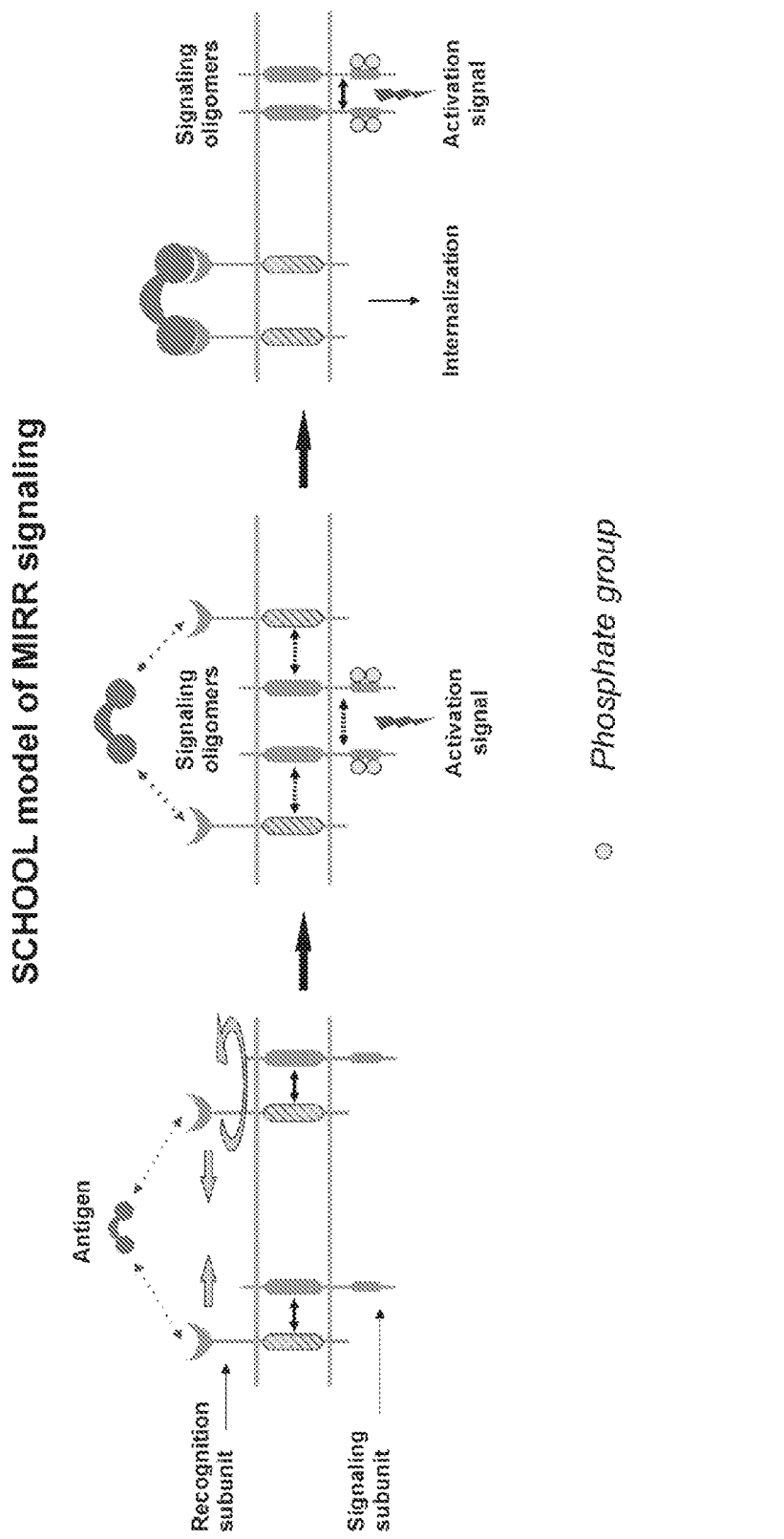
FIG. 1 illustrates one embodiment of a MIRR-mediated transmembrane signal transduction utilizing the signaling chain homooligomerization (SCHOOL) model. The model indicates that the homooligomerization of signaling subunits has a role in triggering MIRR-mediated transmembrane signal transduction. Small unbroken black arrows indicate specific intersubunit hetero- and homointeractions between transmembrane and cytoplasmic domains. Circular arrow indicates ligand-induced receptor reorientation. Although it is not necessary to understand the mechanism of an invention, it is believed that ligand-induced MIRR clustering leads to receptor reorientation and formation of a dimeric or oligomeric intermediate in which signaling chains from different receptor units start to trans-homointeract and form signaling oligomers. All interchain interactions in this intermediate are denoted by broken black arrows, reflecting their transition state. It is further believed that upon the formation of signaling oligomers, protein tyrosine kinases phosphorylate the tyrosine residues in the ITAMs (gray rectangles), leading to transmembrane transduction of activation signal, dissociation of signaling oligomers and internalization of the engaged MIRR-binding domains. Next, the signaling oligomers are believed to sequentially homointeract with the relevant signaling subunits of non-engaged receptors, resulting in the formation of higher signaling oligomers, thus propagating and amplifying the signals (not shown). This may lead to the release and subsequent internalization of the non-engaged ligand-binding domains. A similar general scheme can be considered for the pathway induced by receptor crosslinking, using antibodies to signaling subunits (e.g. anti-CD3e or anti-Igb antibodies for TCRs and BCRs, respectively). Abbreviation: P, phosphate.

The term "myeloid cell-mediated pathology" (or "myeloid cell-related pathologies", or "myeloid cell-mediated disorder, or "myeloid cell-related disease"), as used herein, refers to any condition in which an inappropriate myeloid cell response is a component of the pathology. The term is intended to include both diseases directly mediated by myeloid cells, and also diseases in which an inappropriate myeloid cell response contributes to the production of abnormal antibodies, antibodies, as well as graft rejection.

The term "ligand-induced myeloid cell activation", as used herein, refers to myeloid cell activation in response to the stimulation by the specific ligand.

The term "stimulation", as used herein, refers to a primary response induced by ligation of a cell surface moiety. For example, in the context of receptors, such stimulation entails the ligation of a receptor and a subsequent signal transduction event. With respect to stimulation of a myeloid cell, such stimulation refers to the ligation of a myeloid cell surface moiety that in one embodiment subsequently induces a signal transduction event, such as binding the TREM-1/DAP-12 complex. Further, the stimulation event may activate a cell and up-regulate or down-regulate expression or secretion of a molecule.

The term "ligand", or "antigen", as used herein, refers to a stimulating molecule that binds to a defined population of cells. The ligand may bind any cell surface moiety, such as a receptor, an antigenic determinant, or other binding site present on the target cell population. The ligand may be a protein, peptide, antibody and antibody fragments thereof, fusion proteins, synthetic molecule, an organic molecule (e.g., a small molecule), or the like. Within the specification and in the context of myeloid cell stimulation, the ligand (or antigen) binds the TREM receptor and this binding activates the myeloid cell.

The term "TREM receptor", as used herein, refers to a member of TREM receptor family: TREM-1, TREM-2, TREM-3 and TREM-4.

The term "activation", as used herein, refers to the state of a cell following sufficient cell surface moiety ligation to induce a noticeable biochemical or morphological change. Within the context of myeloid cells, such activation, refers to the state of a myeloid cell that has been sufficiently stimulated to induce production of interleukin 8 (IL-8) and tumor necrosis factor alpha (TNF-alpha), differentiation of primary monocytes into immature dendritic cells, and enhancement of inflammatory responses to microbial products. Within the context of other cells, this term infers either up or down regulation of a particular physico-chemical process.

The term "inhibiting myeloid cell activation" (or "TREM-mediated cell activation"), as used herein, refers to the slowing of myeloid cell activation, as well as completely eliminating and/or preventing myeloid cell activation.

The term, "treating a disease or condition", as used herein, refers to modulating myeloid cell activation including, but not limited to, decreasing cytokine production and differentiation of primary monocytes into immature dendritic cells and/or slowing myeloid cell activation, as well as completely eliminating and/or preventing myeloid cell activation. Myeloid cell-related diseases and/or conditions treatable by modulating myeloid cell activation include, but are not limited to, sepsis, non-small cell lung cancer, inflammatory bowel disease, acute mesenteric ischemia, hemorrhagic shock, rheumatic diseases such, for example, as arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, chronic fatigue syndrome, and other myeloid cell-related inflammatory conditions e.g. myositis, tissue/organ rejection.

The term, "subject" or "patient", as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

The term, "therapeutically effective amount", "therapeutically effective dose" or "effective amount", as used herein, refers to an amount needed to achieve a desired clinical result or results (inhibiting TREM-mediated cell activation) based upon trained medical observation and/or quantitative test results. The potency of any administered peptide or compound determines the "effective amount" which can vary for the various compounds that inhibit myeloid cell activation (i.e., for example, compounds inhibiting TREM ligand-induced myeloid cell activation). Additionally, the "effective amount" of a compound may vary depending on the desired result, for example, the level of myeloid cell activation inhibition desired. The "therapeutically effective amount" necessary for inhibiting differentiation of primary monocytes into immature dendritic cells may differ from the "therapeutically effective amount" necessary for preventing or inhibiting cytokine production.

The term, "agent", as used herein, refers to any natural or synthetic compound (i.e., for example, a peptide, a peptide variant, or a small molecule).

The term, "composition", as used herein, refers to any mixture of substances comprising a peptide and/or compound contemplated by the present invention. Such a composition may include the substances individually or in any combination.

The term, "intrinsic helicity", as used herein, refers to the helicity which is adopted by a peptide in an aqueous solution.

The term, "induced helicity", as used herein, refers to the helicity which is adopted by a peptide when in the presence of a helicity inducer, including, but not limited to, trifluoroethanol (TFE), detergents (e.g., sodium dodecyl sulfate, SDS) or lipids (e.g., lipid vesicles: small and large unilamellar vesicles, SUVs and LUVs, respectively, as described herein).

The term "therapeutic drug", as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars. Drugs or compounds may have any of a variety of activities, which may be stimulatory or inhibitory, such as antibiotic activity, antiviral activity, antifungal activity, steroidal activity, cytotoxic, cytostatic, anti-proliferative, anti-inflammatory, analgesic or anesthetic activity, or can be useful as contrast or other diagnostic agents.

The term "effective dose" as used herein refers to the concentration of any compound or drug contemplated herein that results in a favorable clinical response. In solution, an effective dose may range between approximately 1 ng/ml-100 mg/ml, preferably between 100 ng/ml and 10 mg/ml, but more preferably between 500 ng/ml and 1 mg/ml.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a catheter, syringe etc. A second exemplary method of administering is by a direct mechanism such as, local tissue administration (i.e., for example, extravascular placement), oral ingestion, transdermal patch, topical, inhalation, suppository etc.

The term "anti-inflammatory drug" means any compound, composition, or drug useful for preventing or treating inflammatory disease.

The term "medical device", as used herein, refers broadly to any apparatus used in relation to a medical procedure. Specifically, any apparatus that contacts a patient during a medical procedure or therapy is contemplated herein as a medical device. Similarly, any apparatus that administers a drug or compound to a patient during a medical procedure or therapy is contemplated herein as a medical device. "Direct medical implants" include, but are not limited to, urinary and intravascular catheters, dialysis catheters, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, surgical drapes, sponges and absorbable hemostats. "Surgical devices" include, but are not limited to, surgical instruments, endoscope systems (i.e., catheters, vascular catheters, surgical tools such as scalpels, retractors, and the like) and temporary drug delivery devices such as drug ports, injection needles etc. to administer the medium. A medical device is "coated" when a medium comprising an anti-inflammatory drug (i.e., for example, a variant TREM-1 transmembrane inhibitory peptide) becomes attached to the surface of the medical device. This attachment may be permanent or temporary. When temporary, the attachment may result in a controlled release of a variant TREM-1 transmembrane inhibitory peptide.

The term "endoscope" refers to any medical device that is capable of being inserted into a living body and used for tasks including, but not limited to, observing surgical procedures, performing surgical procedures, or applying medium to a surgical site. An endoscope is illustrated by instruments including, but not limited to, an arthroscope, a laparoscope, hysteroscope, cytoscope, etc. It is not intended to limit the use of an endoscope to hollow organs. It is specifically contemplated that endoscopes, such as an arthroscope or a laparoscope is inserted through the skin and courses to a closed surgical site.

The term "vascular access site" is defined herein as referring to any percutaneous insertion of a medical device into the vasculature. For example, a hemodialysis catheter placement comprises a vascular access site. Such sites may be temporary (i.e., placed for a matter of hours) or permanent (i.e., placed for days, months or years).

The term "vascular graft" as used herein, refers to any conduit or portion thereof intended as a prosthetic device for conveying blood and, therefore, having a blood contacting surface (i.e., "luminal"). While usually in a tubular form, the graft may also be a sheet of material useful for patching portions of the circumference of living blood vessels (these materials are generally referred to as surgical wraps). Likewise, the term vascular graft includes intraluminal grafts for use within living blood vessels. The inventive grafts as such may also be used as a stent covering on the exterior, luminal or both surfaces of an implantable vascular stent.

The term "synthetic vascular graft" as used herein, refers to any artificial tube or cannula designed for insertion into a blood vessel. Such grafts may be constructed from polytetrafluoroethylene (PTFE).

The term "syringe" or "catheter" as used herein, refers to any device or apparatus designed for liquid administration, as defined herein. A syringe or catheter may comprise at least one storage vessel (i.e., for example, a barrel) wherein a single medium resides prior to administration. A syringe or catheter comprising two or more barrels, each containing a separate medium, may mix the media from each barrel prior to administration or the media of each barrel may be administered separately. One of skill in the art will recognize that any catheter designed to perform dialysis, as defined herein, may also administer liquids.

The term "dialysis/apheresis catheter" as used herein, refers to any multi-lumen catheter (i.e., for example, a triple lumen catheter) capable of providing a simultaneous withdrawal and return of blood to a patient undergoing a blood treatment process. Apheresis (called also pheresis) comprises a blood treatment process involving separation of blood elements that can remove soluble drugs or cellular elements from the circulation (Deisseroth et al., in Cancer: Principles And Practice Of Oncology, Devita, V. T. Jr. et al. Editors, Philadelphia: J. B. Lippincott Company 1989, p. 2045-59). For example, blood is withdrawn from a donor, some blood elements (i.e., for example, plasma, leukocytes, platelets, etc.) are separated and retained. The unretained blood elements are then retransfused into the donor.

The term "dialysis catheter" as used herein, refers to any device capable of removing toxic substances (impurities or wastes) from the body when the kidneys are unable to do so. A dialysis catheter may comprise a single catheter having at least a dual lumen (i.e., one lumen withdraws arterial blood and a second lumen returns the dialyzed blood to the venous system) or involve placing two catheters—one that is placed in an artery, and one in an adjacent vein. Dialysis catheters are most frequently used for patients who have kidney failure, but may also be used to quickly remove drugs or poisons in acute situations.

The term "peritoneal dialysis catheter" as used herein, refers to any continuous flow catheters with at least two lumens, one of which is a short lumen (used to infuse a dialysis solution into the peritoneum), and the other of which is a long coiled lumen having a plurality of openings, generally located on the inside of the coil. It is believed that peritoneal solutes enter into the coiled lumen openings and are thereby removed from the peritoneum. One hypothesis suggests that peritoneal dialysis works by using the peritoneal membrane inside the abdomen as the semipermeable membrane. Special solutions that facilitate removal of toxins may be infused in, remain in the abdomen for a time, and then drained out.

The term "fixed split-tip dialysis catheter" as used herein, refers to any catheter having at least two distinct elongated end portions that extend substantially parallel to the longitudinal axis of the catheter and are flexible to the lateral displacement of an infused fluid. It is believed that this flexibility prevents a permanent catheter tip splay that is known to injure tissue. Usually a fixed-tip dialysis catheter provides indwelling vascular access for patients undergoing long-term renal dialysis care (i.e., for example, end-stage renal disease).

The term "femoral catheter" as used herein, refers to any catheter that is inserted into the femoral vein. Femoral catheters are typically provided for intermediate term blood access because the superior vena cava is relatively close to the right atrium of the heart, the minimal range of shape changes of these veins with natural movements of the patient (to minimize the damage to the vessel intima), and because of good acceptance by the patients of the skin exit on the thoracic wall. Further, the femoral veins are easy to cannulate, so that catheters of this invention may be inserted into the femoral veins at the bed side.

The term "attached" as used herein, refers to any interaction between a medium (or carrier) and a therapeutic drug. Attachment may be reversible or irreversible. Such attachment includes, but is not limited to, covalent bonding, and non-covalent bonding including, but not limited to, ionic bonding, Van der Waals forces or friction, and the like. A drug is attached to a medium (or carrier) if it is impregnated, incorporated, coated, in suspension with, in solution with, mixed with, etc. The term "covalent bonding" as used herein, refers to an attachment between two compounds (i.e., for example, a medium and a drug) that comprising a sharing of electrons.

As used herein, the term "peptide" refers to linear or cyclic or branched compounds containing amino acids, amino acid equivalents or other non-amino groups, while still retaining the desired functional activity of a peptide. Peptide equivalents can differ from conventional peptides by the replacement of one or more amino acids with related organic acids such as p35 aminobenzoic acid (PABA), amino acid analogs, or the substitution or modification of side chains or functional groups. Peptide equivalents encompass peptide mimetics or peptidomimetics, which are organic molecules that retain similar peptide chain pharmacophore groups as are present in the corresponding peptide. The term "peptide" refers to peptide equivalents as well as peptides. The amino acids can be in the L or D form so long as the binding function of the peptide is maintained.

As used herein, the term "cyclic peptide" refers to a peptide having an intramolecular bond between two non-adjacent amino acids. The cyclization can be effected through a covalent or non-covalent bond. Intramolecular bonds include, but are not limited to, backbone to backbone, side-chain to backbone and side-chain to side-chain bonds.

As used herein, the term "dimer" as applied to peptides refers to molecules having two peptide chains associated covalently or non-covalently, with or without linkers. Peptide dimers wherein the peptides are linked C-terminus to N-terminus may also be referred to as "tandem repeats" or "tandem dimers." Peptide dimers wherein the peptides are linked C- to C-terminus, or N- to N-terminus may also be referred to as "parallel repeats" or "parallel dimers."

The term "placing" as used herein, refers to any physical relationship (i.e., secured or unsecured) between a patient's biological tissue and a surgical material, wherein the surgical material comprises a pharmaceutical drug that may be, optionally, attached to a medium. Such a physical relationship may be secured by methods such as, but not limited to, gluing, suturing, stapling, spraying, laying, impregnating, and the like. The term "parts by weight", as used herein, when used in reference to a particular component in a composition denotes the weight relationship between the component and any other components in the composition for which a pan by weight is expressed.

The term "protecting groups", as used herein, refer to those groups which prevent undesirable reactions (such as proteolysis) involving unprotected functional groups. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

The term "protein", as used herein, refers to compounds comprising amino acids joined via peptide bonds and includes proteins and polypeptides; and may be an intact molecule, a fragment thereof, or multimers or aggregates of intact molecules and/or fragments; and may occur in nature or be produced, e.g., by synthesis (including chemical and/or enzymatic) or genetic engineering. The terms "protein" and "polypeptide" are used herein interchangeably.

As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include posttranslational modifications of the deduced amino acid sequences, such as amino acid deletions, additions, and modifications such as glycosylation and addition of lipid moieties.

The term "portion" when used in reference to a protein (as in "a portion of a given protein") refers to fragments of that protein. The fragments may range in size from four amino acid residues to the entire amino sequence minus one amino acid.

The term "analog", as used herein, includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The term "conservative substitution", as used herein, also includes the use of a chemically derivatized residue in place of a non-derivatized residue provided that such peptide displays the requisite inhibitory function on myeloid cells as specified herein. The term derivative includes any chemical derivative of the peptide of the invention having one or more residues chemically derivatized by reaction of side chains or functional groups.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as, for example, by the programs SIM+LALNVIEW, LALIGN and DIALIGN using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

It is understood by the person of ordinary skill in the art that the terms "TREM1_HUMAN", "TREM-1 receptor", "TREM-1 receptor subunit", "TREM-1 subunit", and "TREM-1 recognition subunit" refer to the naturally occurring human protein listed in the UniProt Knowledgebase (UniProtKB) under the name "TREM1_HUMAN". The protein amino acid sequence can be found under the entry UniProt KB/Swiss-Prot Q9NP99. It is further understood that the terms "TREM1_Mouse", "mouse TREM-1 receptor", "mouse TREM-1 receptor subunit", "mouse TREM-1 subunit", and "mouse TREM-1 recognition subunit" refer to the naturally occurring mouse protein listed in the UniProt Knowledgebase (UniProtKB) under the name "TREM1_MOUSE". The protein amino acid sequence can be found under the entry UniProt KB/Swiss-Prot Q9JKE2. It is still further understood that the terms "TREM1_Bovin", "bovine TREM-1 receptor", "bovine TREM-1 receptor subunit", "bovine TREM-1 subunit", and "bovine TREM-1 recognition subunit" refer to the naturally occurring bovine protein listed in the UniProt Knowledgebase (UniProtKB) under the name "TREM1_BOVIN". The protein amino acid sequence can be found under the entry UniProt KB/Swiss-Prot Q6QUN5. It is further understood that the terms "TREM1_PIG", "pig TREM-1 receptor", "pig TREM-1 receptor subunit", "pig TREM-1 subunit", and "pig TREM-1 recognition subunit" refer to the naturally occurring pig protein listed in the UniProt Knowledgebase (UniProtKB) under the name "TREM1_PIG". The protein amino acid sequence can be found under the entry UniProt KB/Swiss-Prot Q6TY16.

It is understood by the person of ordinary skill in the art that the terms "TYOBP_HUMAN", "DAP-12", "DAP-12 subunit", and "DAP-12 signaling subunit" refer to the naturally occurring human protein listed in the UniProt Knowledgebase (UniProtKB) under the name "TYOBP_HUMAN". The protein amino acid sequence can be found under the entry UniProt KB/Swiss-Prot O43914. It is further understood that the terms "TYOBP_MOUSE", "mouse DAP-12", "mouse DAP-12 subunit", and "mouse DAP-12 signaling subunit" refer to the naturally occurring mouse protein listed in the UniProt Knowledgebase (UniProtKB) under the name "TYOBP_MOUSE". The protein amino acid sequence can be found under the entry UniProt KB/Swiss-Prot O54885. It is still further understood that the terms "TYOBP_BOVIN", "bovine DAP-12", "bovine DAP-12 subunit", and "bovine DAP-12 signaling subunit" refer to the naturally occurring bovine protein listed in the UniProt Knowledgebase (UniProtKB) under the name "TYOBP_BOVIN". The protein amino acid sequence can be found under the entry UniProt KB/Swiss-Prot Q95J79. It is further understood that the terms "TYOBP_RAT", "rat DAP-12", "rat DAP-12 subunit", and "rat DAP-12 signaling subunit" refer to the naturally occurring rat protein listed in the UniProt Knowledgebase (UniProtKB) under the name "TYOBP_RAT". The protein amino acid sequence can be found under the entry UniProt KB/Swiss-Prot Q6X9T7. It is further understood that the terms "TYOBP_PIG", "pig DAP-12", "pig DAP-12 subunit", and "pig DAP-12 signaling subunit" refer to the naturally occurring pig protein listed in the UniProt Knowledgebase (UniProtKB) under the name "TYOBP_PIG". The protein amino acid sequence can be found under the entry UniProt KB/Swiss-Prot Q9TU45. It is further understood that the terms "Q95KS5_SHEEP", "sheep DAP-12", "sheep DAP-12 subunit", and "sheep DAP-12 signaling subunit" refer to the naturally occurring sheep protein listed in the UniProt Knowledgebase (UniProtKB) under the name "Q95KS5_SHEEP". The protein amino acid sequence can be found under the entry UniProt KB/Swiss-Prot Q95KS5.

DETAILED DESCRIPTION OF THE INVENTION

The peptides and compositions of the present invention are derived from amino acid sequence of transmembrane regions of TREM-1 receptor, can be designed and formulated to be delivered orally, optimized for their efficacy and specificity in accordance to the suggested criteria, thus improving upon prior art and overcoming current limitations in the prior art.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The present invention relates to peptides and compounds which affect the activating TREM receptor signaling pathway in granulocytes, monocytes, macrophages, neutrophils, microglia, dendritic cells, osteoclasts, platelets and other cells. The present invention further relates to the treatment or prevention of cancer, allergic diseases, inflammatory bowel disease, acute mesenteric ischemia, hemorrhagic shock, autoimmune diseases, including but not limited to, rheumatoid arthritis and other rheumatic diseases, sepsis and other inflammatory or other condition involving myeloid cell activation, and, more particularly, TREM receptor-mediated cell activation. Specifically, the peptides and compounds are useful in the treatment and/or prevention of a disease or condition where myeloid cells are involved or recruited. The peptides of the present invention also are useful in the production of medical devices comprising peptide matrices (for example, medical implants and implantable devices). In one embodiment, TREM-1/DAP-12 receptor complex signaling is inhibited by variant peptides binding to the transmembrane region of the DAP-12 subunit.

Various methods of application are proposed to use these protein variants including, but not limited to; i) treating diseases or other medical conditions where myeloid cells are involved or recruited; ii) drug delivery systems; iii) a sequence-based rational drug design method; iv) protease-resistance immunotherapeutic peptides; v) coatings of medical devices, such as implants and implantable devices.

The present invention contemplates constructing a series of variant peptides homologous to a transmembrane core sequence of the triggering receptor expressed on myeloid cells-1 (TREM-1) receptor and capable of reducing said myeloid cell activation by action on the activating TREM-1 receptor. The TREM-1/DAP-12 receptor signaling complex is composed of TREM-1 recognition subunit and a DAP-12 signaling subunit dimer. Thus, TREM-1 is a member of family of multichain immune recognition receptors (MIRRs) which are characterized by a common and distinct receptor architectural feature—their ligand-binding subunits and signaling subunits represent separate transmembrane protein chains that are noncovalently bound in the transmembrane milieu (Sigalov A. B. Trends Immunol 2004; 25:583-9; Sigalov A. B. Adv Exp Med Biol 2008; 640:268-311; Sigalov A. B. Adv Exp Med Biol 2008; 640:121-63; Keegan A. D. & Paul W. E. Immunol Today 1992; 13:63-8). The DAP-12 signaling subunit has a conserved single negative charge in its transmembrane (TM) domain (TABLE 1), while TM domain of the TREM-1 recognition subunit contains one positive charge (TABLE 2). The integrity and functionally of the receptor is provided by the TM electrostatic interactions. The positively charged Lys residue in the TM region of the TREM-1 chain interacts with the negatively charged Asp residues of the TM domains of DAP-12 homodimer. Assembly of other TREM receptors is similar. Recently, these interactions have been suggested as universal therapeutic targets for a diverse variety of pathologies (Sigalov A. B. Trends Immunol 2004; 25:583-9; Sigalov A. B. Adv Exp Med Biol 2007; 601:335-44).

The TREM-1/DAP-12-coupled receptor signaling pathway resident within myeloid cell membranes represents but one mechanism responsible for myeloid cell activation. Although it is not necessary to understand the mechanism of an invention, it is believed that these variant peptides insert themselves into the cell membrane and act as a "receptor decoy" for TREM ligand molecules. It is further believed that TREM-1/DAP-12-mediated cell activation requires the bridging of multiple TREM-1/DAP-12-coupled receptors that generates an intracellular activation signal by bringing membrane-embedded DAP-12 subunits into close proximity and correct (permissive) orientation. These TREM-1-like peptide variants may prevent cell activation by reducing DAP-12-DAP-12 aggregation by generating TREM-1/DAP-12/peptide variant bridges in the presence of ligand. It is further believed that the molecular basis for the prevention of myeloid cell activation is based upon protein-protein interactions.

Protein-protein interactions are involved in most biological processes and thus represent an appealing target for innovative drug development. These interactions can be targeted by small molecule inhibitors, peptides, and peptidomimetics. Consequently, indirect protein therapy that alters protein-protein interactions represents an alternative to direct protein therapeutics (i.e., for example, immunotherapy) and avoids dangerous side effects. Indirectly acting peptides may serve as active regulators and participate in molecular cross talk, which drives metabolic processes. These indirectly acting peptides are also extremely potent, showing high specificity, and have few toxicological problems. Moreover, these indirectly acting peptides do not accumulate in organs or suffer from drug-drug interactions as many small molecules do. They can be used as therapeutic agents, or as a starting point for developing peptidomimetics and small molecular weight inhibitors.

1. Triggering Receptors Expressed on Myeloid Cells

The myeloid lineage gives rise to cells that function both in the immune system and in remodeling host tissue (Klesney-Tait et al. Nat Immunol 2006; 7:1266-73). The differentiation and activation of those cells is regulated by signals received through the cell surface and intracellular receptors that recognize both soluble and surface-expressed ligands. Those receptors can be broadly classified into two groups: those 'tasked' to recognize a specific event, and those through which the cell receives more general information about the state of the organism. Examples of the former include the Toll-like receptors (TLRs), which signal the presence of a microbial pathogen, and growth factor receptor, which drives differentiation. Those task-specific receptors determine the qualitative nature of the response of the cells, such as activation or differentiation. In contrast, stimulation of receptors in the second group (those that 'read out' the state of the organism) does not by itself induce a substantial response by the cell but instead helps to set thresholds for the cellular response to specific stimuli and to modulate the magnitude of that response. By integrating the responses of both groups of receptors, the cell can generate a carefully graded response to a specific set of conditions.

TREM proteins ('triggering receptors expressed on myeloid cells') are a family of cell surface receptors expressed broadly on myeloid cells. The first TREM identified (TREM-1) was characterized as an amplifier of the immune response that strongly potentiates the activation of leukocytes in response to microbial products. The TREM family has since been extended to include proteins expressed on granulocytes, monocytes, macrophages, microglia, dendritic cells, osteoclasts and platelets. Generally, these receptors seem to function mainly as modulators of the cellular response, falling squarely into the second group of receptors (those that set 'thresholds' for cells) described above. By coordinating diverse stimuli, TREM proteins have both positive and negative functions in regulating the activation and differentiation of myeloid cells.

The TREM family includes at least two activating receptors, namely TREM-1 and TREM-2 which are transmembrane glycoproteins with a single extracellular Ig-like domain, a transmembrane region with a charged Lys residue, and a short intracellular region (Gibot S. Crit Care 2005; 9:485-9). Engagement of TREMs, after association with the signaling adapter protein DAP12 (which contains an immunoreceptor tyrosine-based activation motif, ITAM), triggers a signaling pathway involving ζ-chain-associated protein 70 (ZAP70) and spleen tyrosine kinase. This in turn leads to the recruitment and tyrosine phosphorylation of adaptor molecules such as growth factor receptor binding protein 2, and activation of phosphatidylinositol 3-kinase, phospholipase C-gamma, extracellular signal regulated kinase-1 and -2, and p38 mitogen-associated protein kinase. Activation of these pathways leads to intracellular calcium mobilization, actin cytoskeleton rearrangement, and activation of transcription factors. TREM-1 has been implicated in mounting the inflammatory response, whereas TREM-2 regulates dendritic cells, osteoclasts and microglia.

TREM receptors are attractive targets for therapy of myeloid cell-related pathologies. TREM-1 seems particularly attractive in this respect. Since its detection, the function of TREM-1 and the signal transduction pathway induced by the TREM-1/DAP-12 receptor signaling complex have been extensively studied. The selective inhibition of TREM-1 and/or its signaling is thought by most workers in the field to provide new promising therapeutic strategies to fight myeloid cell-mediated disease (Bouchon et al. J Immunol 2000; 164:

4991-5; Bouchon et al. Nature 2001; 410:1103-7; Gibot S. Crit Care 2005; 9:485-9; Gibot et al. J Exp Med 2004; 200: 1419-26; Gibot et al. Shock 2009; 32:633-7; Ling et al. Chinese Med J 2010; 123:1561-5; Gibot et al. Crit Care Med 2008; 36:504-10; Klesney-Tait et al. Nat Immunol 2006; 7:1266-73; Murakami et al. Arthritis Rheum 2009; 60:1615-23; Sharif O. & Knapp S. Immunobiology 2008; 213:701-13). In addition, recent findings have linked TREM-1 to non-small cell lung cancer (NSCLC) (Ho et al. Am J Respir Crit Care Med 2008; 177:763-70) and inflammatory bowel disease (IBD) (Ford J. W. & McVicar D. W. Curr Opin Immunol 2009; 21, 38-46).

Currently, very few approaches have pursued an inhibition of TREM-1-mediated transmembrane signaling. Antibodies that specifically recognize TREM-1 were used to prevent ligand binding and initiation of cell aggregation (US Pat Appl 20080247955; Piccio et al. Eur J Immunol 2007; 37, 1290-301; herein incorporated by reference in their entirety). Fusion proteins between human IgG1 constant region and the extracellular domain of mouse TREM-1 or that of human TREM-1 were also suggested to prevent ligand binding (US Pat Appls 20090081199 and 20030165875). However, these large protein molecules pose serious disadvantages.

Peptides based on TREM-1-derived sequences for disrupting TREM-1 function presumably by blocking binding of the receptor with its cognate ligand have also been disclosed (US Pat Appl 20060246082) or published (Murakami et al. Arthritis Rheum 2009; 60:1615-23; Gibot et al. Crit Care Med 2008; 36:504-10; Gibot et al. Shock 2009; 32:633-7). Despite multiple advantages of these peptides as compared to antibodies, they have relatively low efficacy in terms of inhibiting TREM-1, thus having a high potential for toxicity and side effects. For example, the systemic administration of a synthetic antagonistic TREM-1 peptide that mimics short highly interspecies-conserved extracellular domains of TREM-1 and is often called as LP-17 suppresses collagen-induced arthritis, although the effect is not as complete as that observed following viral gene transfer (Murakami et al. Arthritis Rheum 2009; 60:1615-23).

2. SCHOOL Model of TREM Signaling

Further development of effective therapeutic agents which prevent TREM-mediated cell activation depends on an improved understanding of the TREM-1/DAP-12-coupled receptor signaling pathway. Upon stimulation by ligand, TREM-1 signals through a noncovalently associated DAP-12, a transmembrane protein that mediates signaling through its ITAM.

In this regard, a TREM-1 receptor is a member of the MIRR family, members of which are multisubunit complexes formed by the association of recognition subunits with ITAM-containing signaling subunits. This association in resting cells is mostly driven by the noncovalent transmembrane interactions between recognition and signaling components and plays a role in receptor assembly and integrity. Ligand binding results in phosphorylation of the ITAM tyrosines, which triggers the elaborate intracellular signaling cascade. The mechanism linking extracellular clustering of MIRR ligand-binding subunits to intracellular phosphorylation of signaling subunits remains to be identified. In this regard, the mechanisms of TREM-1 transmembrane signaling has been also elusive, thus hindering the further development of promising therapeutic strategies for the treatment/prophylaxis of myeloid cell-mediated disease.

Therapeutic strategies contemplated herein involve MIRR triggering and subsequent signaling. MIRR-mediated signal transduction, their role in health and disease, and the use of these receptors as attractive targets for rational drug design efforts in the treatment of several immune disorders are described in (US Pat Appl 20090075899; Sigalov A. Semin Immunol 2005; 17:51-64; Sigalov A. B. Trends Immunol 2004; 25:583-9; Sigalov A. B. Trends Pharmacol Sci 2006; 27:518-24; Sigalov A. B. Adv Exp Med Biol 2007; 601:335-44; Sigalov A. B. Adv Exp Med Biol 2008; 640:268-311) which are incorporated herein by reference in their entirety.

Figure 2:
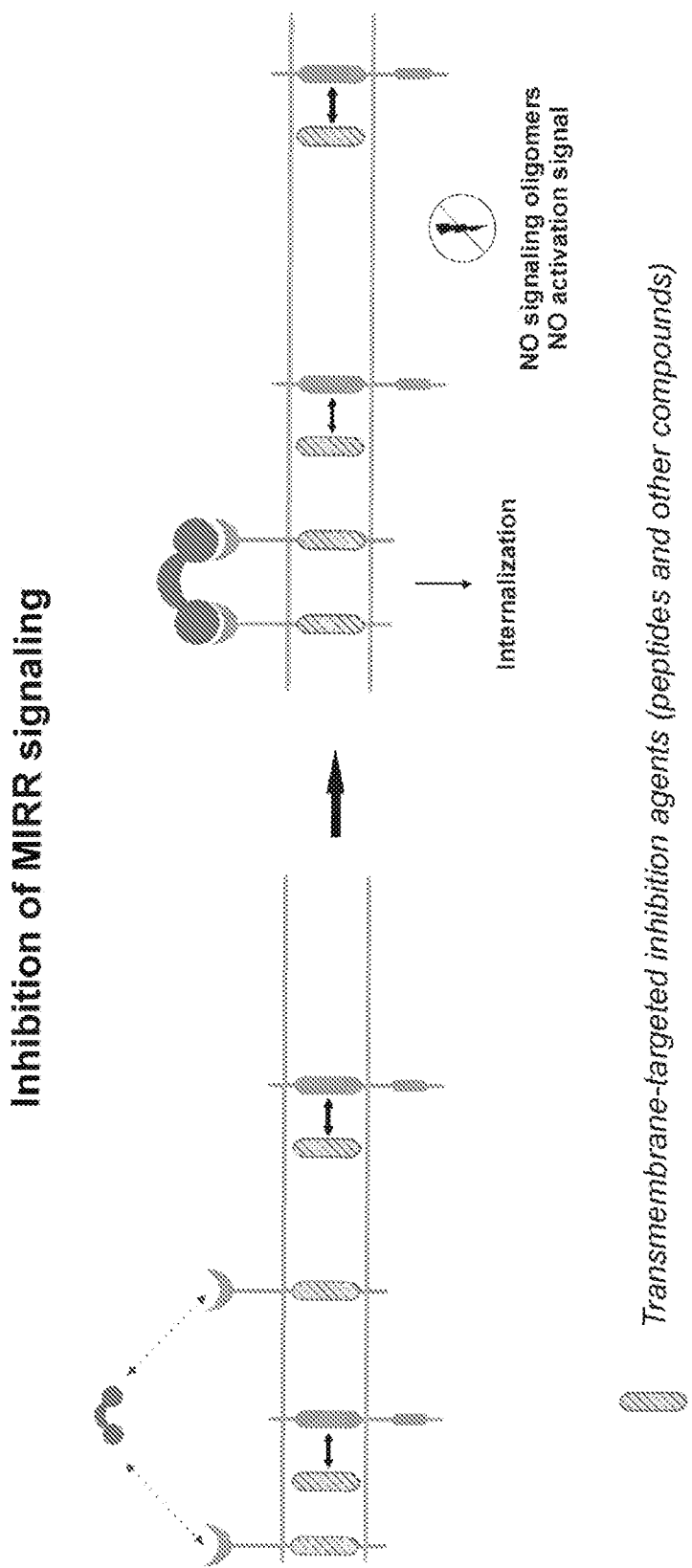
FIG. 2 illustrates one embodiment of a specific blockade of transmembrane interactions between recognition and signaling subunits resulting in "pre-dissociation" of the receptor complex, thus preventing formation of signaling oligomers and inhibiting antigen-dependent immune cell activation.

In one embodiment, the present invention contemplates therapeutic targets compatible with a novel model of MIRR signaling; the Signaling Chain HomO-OLigomerization (SCHOOL) model (See FIG. 1) (Sigalov A. B. Trends Immunol 2004; 25:583-9; Sigalov A. B. Trends Pharmacol Sci 2006; 27:518-24; Sigalov A. B. Adv Exp Med Biol 2008; 640:268-311; Sigalov A. B. Adv Exp Med Biol 2008; 640: 121-63; incorporated herein by reference in their entirety). Although it is not necessary to understand the mechanism of an invention, it is believed that the structural similarity of the MIRRs provides the basis for the similarity in the mechanisms of MIRR-mediated signaling (FIG. 1). It is also believed that the model reveals MIRR transmembrane interactions as new therapeutic targets (See FIG. 2). It is further believed that a general pharmaceutical approach based upon this SCHOOL model can be used to treat diverse immune-mediated diseases.

Figure 3:
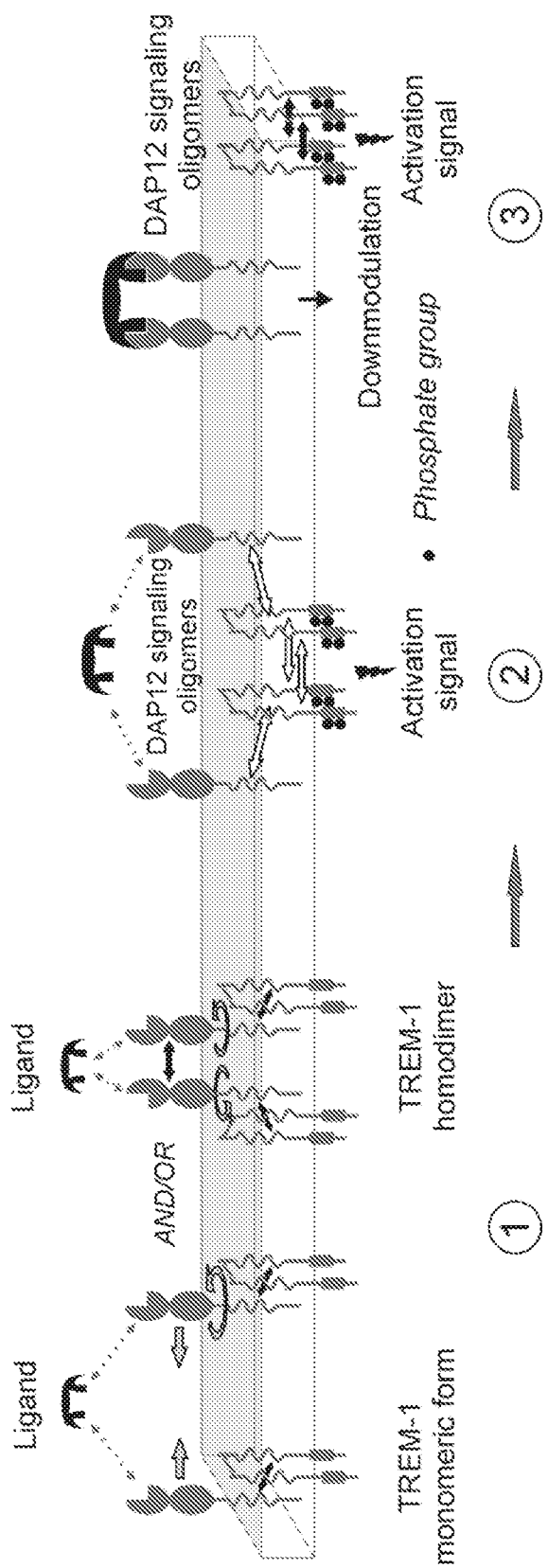
FIG. 3 illustrates one embodiment of a SCHOOL model of TREM-1-mediated transmembrane signal transduction and its inhibition. Solid arrows: Specific subunit homointeractions between cytoplasmic domains.
Figure 4:
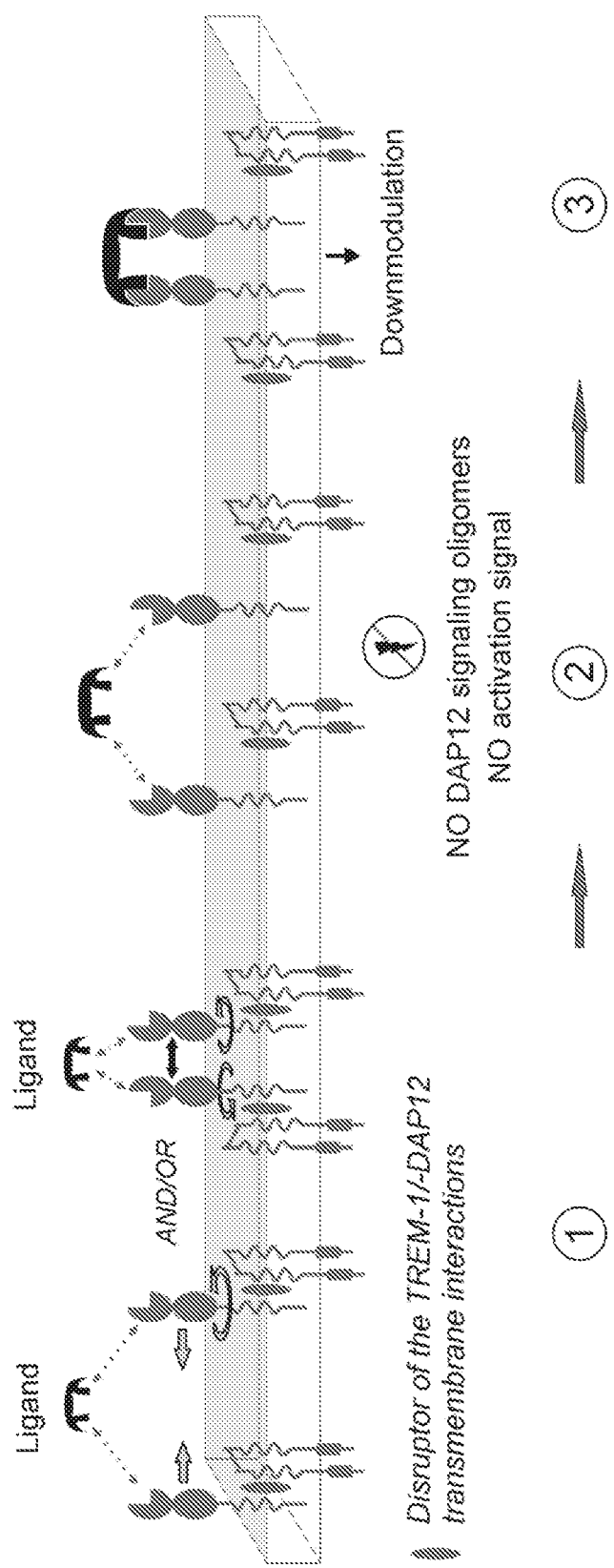
FIG. 4 illustrates one embodiment of a specific blockade of transmembrane interactions between TREM-1 and DAP-12 resulting in "pre-dissociation" of a receptor complex.

Application of the SCHOOL model to the transmembrane signal transduction mediated by a TREM receptor (i.e., for example, TREM-1) (FIG. 3) suggested that an inhibition of TREM-1/DAP-12 signaling may be achieved by using transmembrane-targeted agents which specifically disrupt transmembrane interactions between TREM-1 and DAP-12 subunits (FIG. 4). For example, the simplest agents would be synthetic peptides corresponding to the TREM-1 transmembrane domain. Without being limited by a particular theory, the basic principles of one proposed mechanism by which peptides and other compound of the present invention may work by TREM-1-mediated transmembrane signaling. See, FIGS. 4, 5, and 6.

It is believed that ligand-induced clustering of a TREM-1/DAP-12 receptor complex leads to formation of DAP-12 signaling oligomers with subsequent phosphorylation of the ITAM Tyr residues and cell activation. See, FIG. 3. This hypothesis suggests that a TREM-1 Core Peptide (TREM-1-CP), a peptide corresponding to the transmembrane region of TREM-1, inserts into the cell membrane and competitively binds to the transmembrane domain of DAP-12 chain, thus displacing a TREM-1 receptor from interacting with a signaling DAP-12 subunit, thereby resulting in a "pre-dissociation" of a TREM-1/DAP-12 receptor complex. As a consequence, ligand-induced TREM-1 clustering does not lead to formation of DAP-12 signaling oligomers and subsequent cell activation. See, FIG. 4.

Normal transmembrane interactions between the TREM-1 and the DAP-12 dimer forming a functional TREM-1/DAP-12 receptor complex comprise positively charged lysine amino acid within the TREM-1 transmembrane portion and negatively charged aspartic acid pairs in a DAP-12 dimer, thereby allowing subunit association. See FIG. 5. Although it is not necessary to understand the mechanism of an invention, it is believed that interactions between a lysine residue of a TREM-1 core peptide inhibitor and an aspartic acid residue of a DAP-12 dimer disrupt the transmembrane interactions between TREM-1 and DAP-12, thereby "disconnecting" TREM-1 and resulting in a non-functioning receptor. See FIG. 6.

3. TREM-1 Peptides and Variants Thereof

Although it is not necessary to understand the mechanism of an invention, it is believed that a hydrophobic/polar/charged amino acid sequence patterning, rather than sequence similarity, within the transmembrane TREM-1 domain plays a dominant role in the development of effective peptide-based inhibitors of TREM-1-mediated cell activation. For example, despite the lack of sequence similarity, the fusion peptide (FP) in the N terminus of the HIV envelope glycoprotein 41, inhibit T cell receptor (TCR)-mediated T cell activation in vitro and in vivo in a similar way but more effectively than the transmembrane TCR core peptide (CP) with 100-fold lower the 50% inhibitory concentration (IC50) values for FP than those observed for CP.

In some embodiments, as contemplated by the present invention, optimal peptide inhibitors and peptide inhibitor analogues are designed using hydrophobic/polar/charged sequence pattern criteria and associated evaluation techniques. These peptide inhibitors may then be synthesized and tested in cell function inhibition assays and in animal studies.

Listed below in Table 1 are reported transmembrane sequences of TREM-1 and DAP-12 in a number of species. These regions are highly conserved and the substitutions between species are very conservative. This suggests a functional role for the transmembrane regions of both, TREM-1 and DAP-12, constituents of the complex. These regions strongly interact between themselves, thus maintaining the integrity of the TREM-1/DAP-12 receptor signaling complex in resting cells. These transmembrane domains are short and should be easily mimicked by synthetic peptides and compounds. Based on these features, and taking advantage of the SCHOOL model of MIRR signaling to explain TREM-1-mediated cell activation, the present invention contemplates a new approach of intervening and modulating TREM-1 function. In some embodiments, synthetic peptides and compounds are contemplated that may provide successful treatment options in the clinical setting.

necessary to understand the mechanism of an invention, it is believed that this inhibition is mediated by disrupting the transmembrane interactions between the recognition, TREM-1, and signaling, DAP-12, subunits. In other embodiments, these peptide inhibitors treat and/or prevent diseases and/or conditions comprising activation of TREM-expressing myeloid cell. In one embodiment, the peptide inhibitors modulate TREM-1-mediated cell activation. In another embodiment, the present invention contemplates a drug delivery system (e.g., as disclosed in US Pat Appl 20080193375 and incorporated herein by reference in its entirety) comprising peptide inhibitors of the present invention. As disclosed in PCT Appl. No. PCT/US2010/52117 "Methods and Compositions for Targeted Imaging" the entire content of which is incorporated herein by reference, in various configurations, a drug delivery composition can also comprise lipoprotein nanoparticles wherein said nanoparticles comprise at least one modified apolipoprotein and at least one lipid. Although it is not necessary to understand the mechanism of an invention, it is believed that the peptide inhibitor drug delivery system functions by penetrating the cell membrane.

Sequence-based rational design can be used as a tool in order to increase the effectiveness of the peptides to inhibit the function of the TREM-1/DAP-12 receptor complex. For example, a conservative amino acid substitution of lysine for arginine or insertion of at least one supplemental positively charged amino acid residue (i.e., for example, arginine and/or

TABLE 1

Sequence comparison of TREM-1 and DAP-12 transmembrane regions (accession codes are given in parenthesis)

| SPECIES | TREM-1 | DAP-12 |
|---|---|---|
| HUMAN: (O43914) | IVILLAGGFLSKSLVFSVLFA (Q9NP99) | GVLAGIVMGDLVLTVLIALAV |
| MOUSE: (O54885) | VTISVICGLLSKSLVFIILFI (Q9JKE2) | GVLAGIVLGDLVLTLLIALAV |
| BOVIN: (Q95J79) | IIIPAACGLLSKTLVFIGLFA (Q6QUN5) | GVLAGIVLGDLMLTLLIALAV |
| SHEEP: (Q95KS5) | not known | GVLAGIVLGDLMLTLLIALAV |
| RAT: (Q6X9T7) | not known | GVLAGIVLGDLVLTLLIALAV |
| PIG: (Q9TU45) | ILPAVCGLLSKSLVFIVLFVV (Q6TYI6) | GILAGIVLGDLVLTLLIALAV |

| CLUSTAL W 2.0 multiple sequence alignment: | | |
|---|---|---|
| HUMAN | IVILLAGGFLSKSLVFSVLFA- 21 | GVLAGIVMGDLVLTVLIALAV 21 |
| MOUSE | VTISVICGLLSKSLVFIILFI- 21 | GVLAGIVLGDLVLTLLIALAV 21 |
| BOVIN | IIIPAACGLLSKTLVFIGLFA- 21 | GVLAGIVLGDLMLTLLIALAV 21 |
| SHEEP | — | GVLAGIVLGDLMLTLLIALAV 21 |
| RAT | — | GVLAGIVLGDLVLTLLIALAV 21 |
| PIG | -ILPAVCGLLSKSLVFIVLFVV 21 | GILAGIVLGDLVLTLLIALAV 21 |
| | :  *:*:* ** | *:***:*::**** |

In one embodiment, the present invention contemplates a series of peptides that are inhibitors of a TREM receptor (i.e., for example, a TREM-1/DAP-12 complex) Although it is not lysine) may be made in certain locations on α-helixes of TREM-1 core or extended peptides. Although it is not necessary to understand the mechanism of an invention, it is believed that these changes should result in increased binding activity to the transmembrane domain of the DAP-12 signaling subunit dimer, thus enhancing the effectiveness of the peptides to inhibit the function of an TREM-1/DAP-12 receptor complex. See FIG. 7.

TREM-1 peptide inhibitors and variants thereof contemplated herein may be modified at the carboxy terminal without loss of activity. Accordingly, it is intended that the present invention includes within its scope, peptides which include additional amino acids to the "core" sequence of the peptide of the present invention and which affect the interaction of TREM-1 and DAP-12 subunits of the TREM-1/DAP-12 complex (i.e., for example, an Extended Peptide).

In some embodiments, the peptide inhibitors comprise D-stereoisomeric amino acids, thereby allowing the formulation of immunotherapeutic peptides with increased resistance to protease degradation. In one embodiment, the D-amino acid peptide inhibitors are used for the clinical treatment in myeloid cell-mediated disorders. Although it is not necessary to understand the mechanism of an invention, it is believed that these peptide inhibitors prevent activation of TREM-expressing myeloid cells.

In some embodiments, the present invention contemplate peptide inhibitors that are protease resistant. In one embodiment, such protease-resistant peptide inhibitors are peptides comprising protecting groups. For example, a peptide may be protected from exoproteinase degradation by N-terminal acetylation ("Ac") and/or C-terminal amidation.

In some embodiments, the peptide inhibitors comprise conjugated lipids and/or sugars. In other embodiments, the peptide inhibitors comprise hydrophobic amino acid motifs, wherein said motifs are known to increase the membrane penetrating ability of peptides and proteins. Although it is not necessary to understand the mechanism of an invention, it is believed that either lipid/sugar conjugation and/or hydrophobic amino acid motifs increase the efficacy of TREM-1 inhibition using either TREM-1 Core Peptides and/or Extended Peptides.

In some embodiment, the peptides and compounds contemplated by the present invention may be used for production of peptide/compound-containing implants or implantable devices.

4. TREM-1 Transmembrane Segments

A. Transmembrane Peptide Variants for Inhibition of TREM-1 Signaling

The present invention described herein relates to unknown synthetic peptides and derivatives thereof, which may be useful in the clinical treatment and/or prevention of myeloid cell-mediated disorders.

Figure 8:
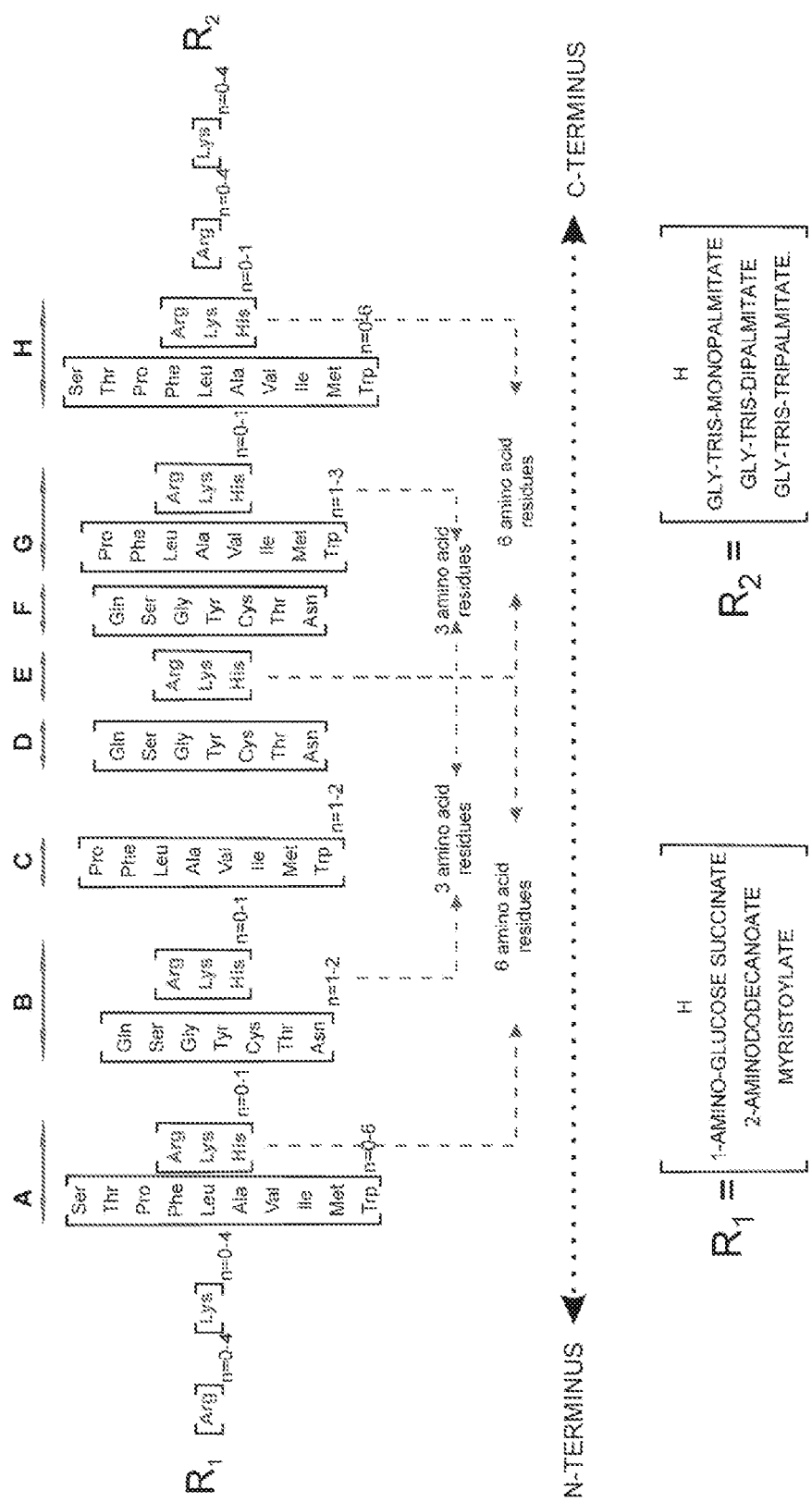
FIG. 8 presents various embodiments of TREM-1 peptide inhibitor sequences based upon a general formula, wherein in the general formula describes variants of the parent TREM-1 transmembrane sequence.
Figure 9:
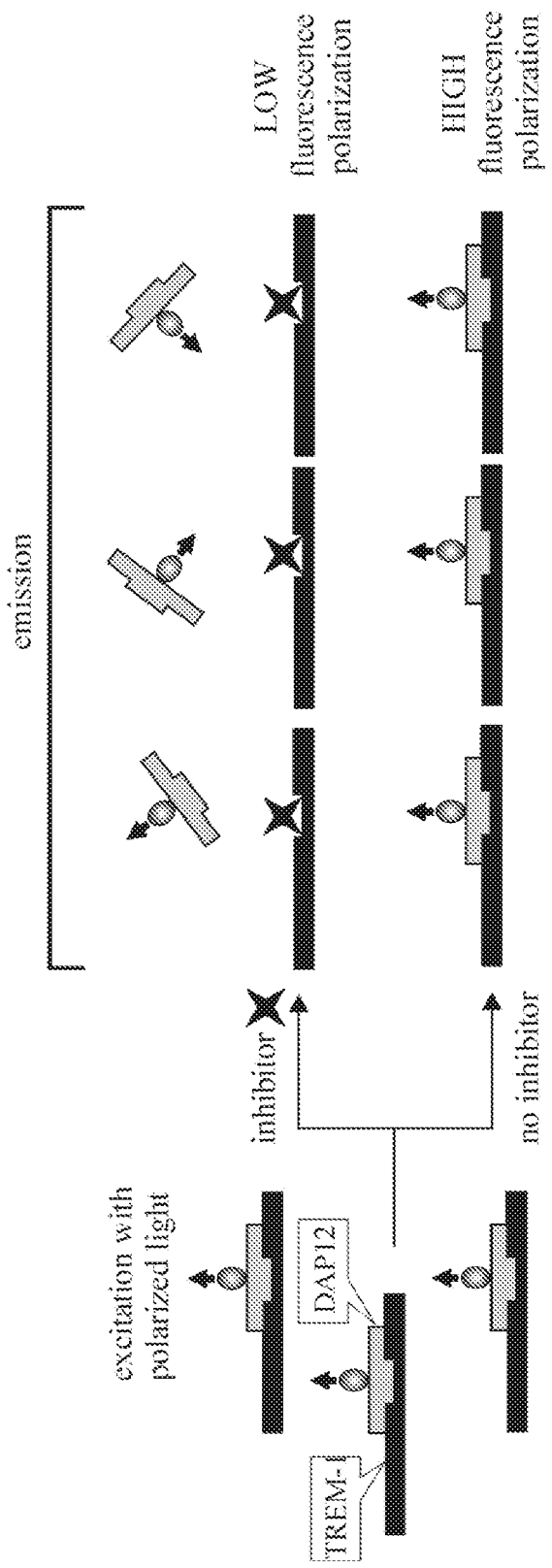
FIG. 9 shows one embodiment of a fluorescence polarization assay that could be used in high-throughput screening strategies to identify both peptide and nonpeptide inhibitors of protein-protein interaction between TREM-1 and DAP-12 subunits of the TREM-1/DAP-12 signaling complex. Gray oval: fluorophore; Arrow: transition vector of fluorescence emission.
Figure 10:
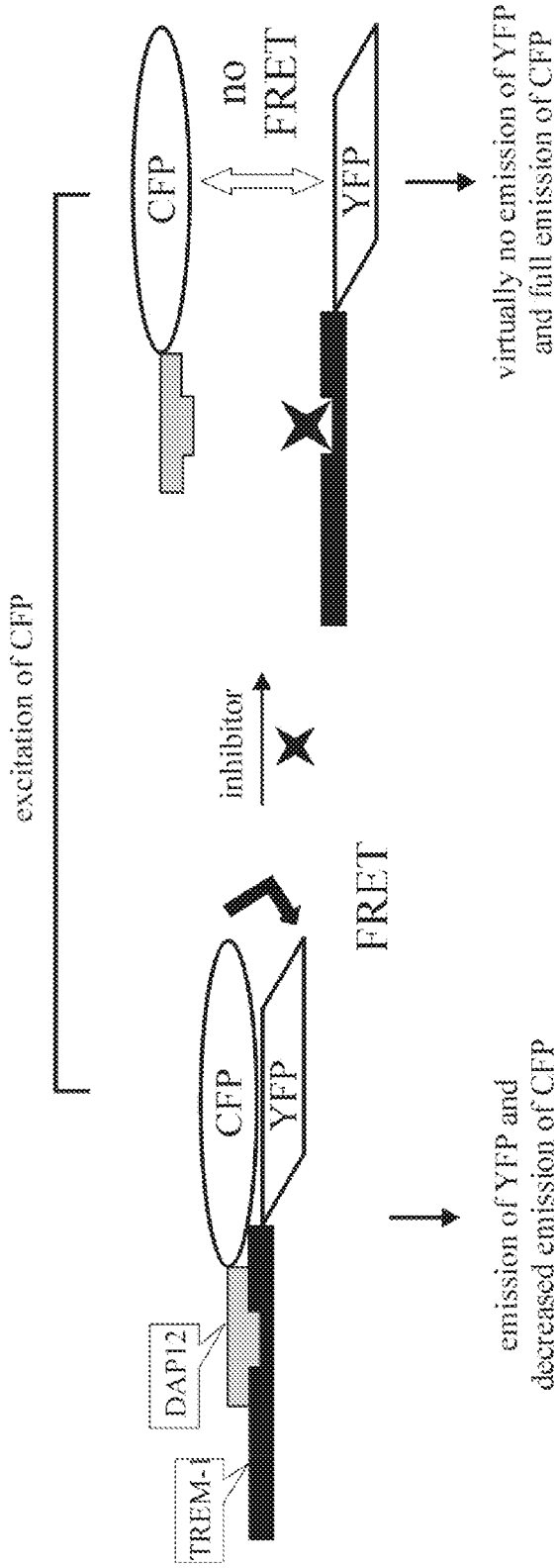
FIG. 10 shows one embodiment of a fluorescence resonance energy transfer (FRET) assay that could be used in high-throughput screening strategies to identify both peptide and non-peptide inhibitors of protein interactions between TREM-1 and DAP-12 subunits of the TREM-1/DAP-12 signaling complex. CFP: cyan fluorescent protein; YFP: yellow fluorescent protein.
Figure 11:
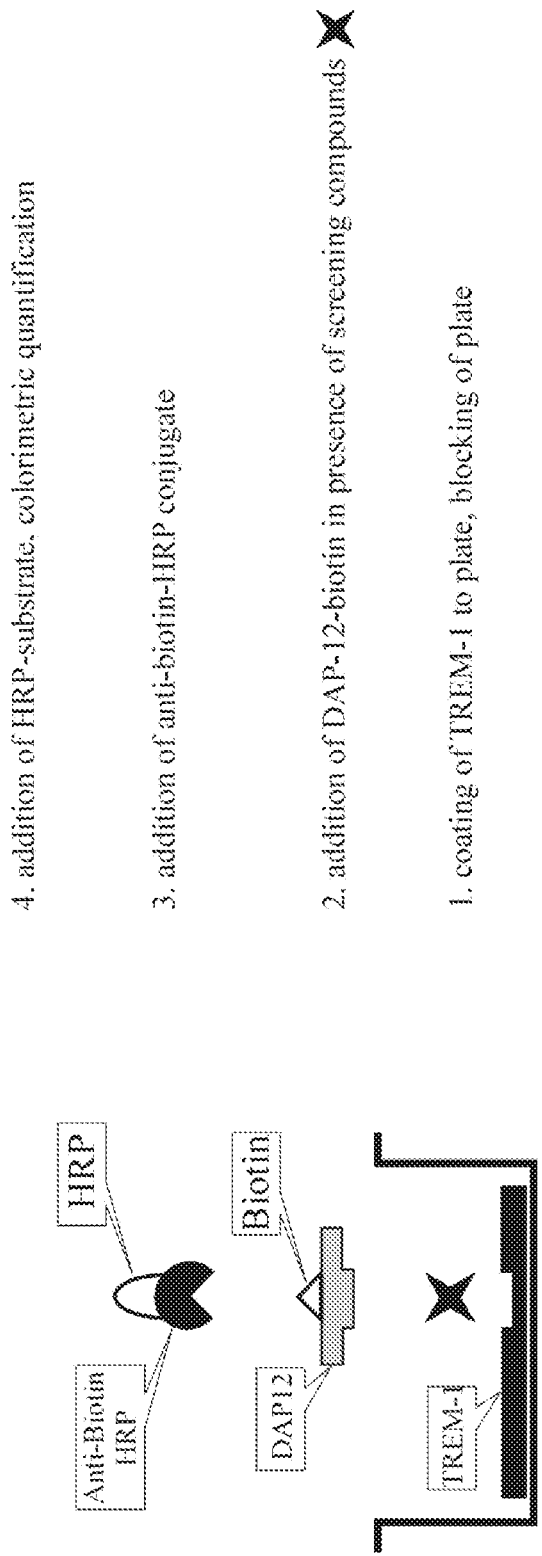
FIG. 11 shows one embodiment of an enzyme-linked immunosorbent assay (ELISA) that could be used in high-throughput screening strategies to identify both peptide and nonpeptide inhibitors of protein-protein interaction between TREM-1 and DAP-12 subunits of the TREM-1/DAP-12 signaling complex. HRP: horseradish peroxidase.

In one embodiment, the present invention contemplates a peptide derivative having the general formula $R_1$-A-B-C-D-E-F-G-H-$R_2$ (See FIG. 8) or a disulfide-bridged, linear dimer thereof, or a cyclic dimer thereof, wherein:

A is absent, Ser, Thr, or a peptide consisting of 1 to 6 hydrophobic uncharged D- or L-amino acids, or a peptide consisting of 1 to 6 hydrophobic uncharged D- or L-amino acids surrounding a positively charged D- or L-amino acid which is spaced 6 amino acids from E;

B is a peptide consisting of 1 to 2 non-hydrophobic uncharged D- or L-amino acids, including D- or L-cysteine or a D- or L-cysteine homologue, or a peptide consisting of 1 to 2 non-hydrophobic uncharged D- or L-amino acids, including D- or L-cysteine or a D- or L-cysteine homologue surrounding a positively charged D- or L-amino acid which is spaced 3 amino acids from E;

C is a peptide consisting of 1 to 2 hydrophobic uncharged D- or L-amino acids;

D is a non-hydrophobic uncharged D- or L-amino acid, including D- or L-cysteine or a D- or L-cysteine homologue;

E is a positively charged D- or L-amino acid;

F is a non-hydrophobic uncharged D- or L-amino acid, including D- or L-cysteine or a D- or L-cysteine homologue;

G is a peptide consisting of 1 to 3 hydrophobic uncharged D- or L-amino acids, or a peptide consisting of 1 to 3 hydrophobic uncharged D- or L-amino acids surrounding a positively charged D- or L-amino acid which is spaced 3 amino acids from E;

H is absent, Ser, Thr, or a peptide consisting of 1 to 6 hydrophobic uncharged D- or L-amino acids, or a peptide consisting of 1 to 6 hydrophobic uncharged D- or L-amino acids surrounding a positively charged D- or L-amino acid which is spaced 6 amino acids from E;

$R_1$ is absent (i.e., for example, —H) or 1-amino-glucose succinate, 2-aminododecanoate, or myristoylate; and $R_2$ is absent (i.e, for example, —H) or Gly-Tris-monopalmitate, -dipalmitate and -tripalmitate.

In some embodiments, peptide derivatives are created wherein:

A is selected from the group comprising Ser, Leu, Val, Ala, Arg, and Lys;

B is selected from the group comprising Gln, Ser, Gly, Cys, and Arg;

C is selected from the group comprising Pro, Phe, Ala and Leu;

D is selected from the group comprising Ser, Gly, and Thr;

E is selected from Arg or Lys;

F is selected from the group comprising Ser, Gly, and Thr;

G is selected from the group comprising Leu, Val, and Phe; and

H is selected from the group comprising Ile, Ser, Leu, Val, Phe, and Ala.

In one embodiment, the present invention contemplates a peptide derivative having the general formula $R_1$-[Arg and/or Lys]$_{n=0-4}$-A-B-C-D-E-F-G-H-[Arg and/or Lys]$_{n=0-4}$-$R_2$ or a disulfide-bridged, linear dimer thereof, or a cyclic dimer thereof, wherein:

A may be i) absent; ii) 1-7 amino acids selected from the group including, but not limited to, Gln, Ser, Gly, Tyr, Cys, Thr, Asn, Lys, Arg, Lys, or Gln, or iii) 1-7 amino acids selected from the group including, but not limited to, Pro, Phe, Leu, Ala, Val, Ile, Met, Arg, Lys, or Trp;

B may be 1-3 amino acids selected from the group including, but not limited to, Ser, Gly, Tyr, Cys, Thr, Asn, Lys, Arg, Lys, or Gln;

C may be 1-2 amino acids selected from the group including, but not limited to, Pro, Phe, Leu, Ala, Val, Ile, Met, Trp, or Cys;

D may be selected from the group including, but not limited to, Gln, Ser, Gly, Tyr, Cys, Ile, and Asn;

E may be selected from the group including, but not limited to, Arg, Lys, and His;

F may be selected from the group including, but not limited to, Gln, Ser, Gly, Tyr, Cys, Ile, and Asn;

G may be 1-4 amino acids selected from the group including, but not limited to, Pro, Phe, Leu, Ala, Val, Ile, Met, Trp, Arg, or Lys;

H may be i) absent; ii) 1-7 amino acids selected from the group including, but not limited to, Gln, Ser, Gly, Tyr, Cys, Thr, Asn, Lys, Arg, Lys, or Gln, or iii) 1-7 amino acids selected from the group including, but not limited to, Pro, Phe, Leu, Ala, Val, Ile, Met, Arg, Lys, or Trp;

$R_1$ and $R_2$ may be either i) absent; ii) a conjugated lipid selected from the group including, but not limited to, Gly-Tris-monopalmitate, -dipalmitate and -tripalmitate; or iii) a conjugated sugar selected from the group including, but not limited to, 1-amino-glucose succinate, 2-aminododecanoate, or myristoylate. See, FIG. 8.

As referred to herein, hydrophobic amino acids include, but are not limited to, Ala, Val, Leu, Ile, Pro, Phe, Trp, and Met; positively charged amino acids include, but are not limited to, Lys, Arg and His; and negatively charged amino acids include, but are not limited to, Asp and Glu.

The general formula above represents one embodiment of a TREM-1 transmembrane segment comprising at least one conserved domain that contains highly homologous sequences between species. In one embodiment, a TREM-1 transmembrane segment comprises GFLSKSLVF (Gly-Phe-Leu-Ser-Lys-Ser-Leu-Val-Phe; human amino acid residues 213-221; Accession No. Q9NP99) along with various lipid and/or sugar derivatives that may, or may not, have a disulfide bridged dimer. In another embodiment, a TREM-1 transmembrane segment comprises KKILLAGGFLSKSLVRSV-LFAKR, wherein said sequence meets the criteria for the above outlined general formula.

In one embodiment, the present invention contemplates a method of rational designing of the peptides and lipid- and/or sugar-conjugated peptides consisting of L- or D-stereoisomeric amino acids in order to increase effectiveness of the peptides in inhibiting the function of a TREM-1/DAP-12 receptor complex. In one embodiment, the method comprises substituting at least one amino acid of a TREM-1 transmembrane core peptide (i.e., for example, and arginine or a lysine into at least one alpha-helix of the Peptide Core and/or Extended Peptide), thereby increasing binding to the transmembrane domain of DAP-12 chain. See, FIG. 7.

In another embodiment, the method comprises conjugating at least one lipid and/or at least one sugar to the C- and/or N-termini of the peptide, thereby increasing binding to the transmembrane domain of the DAP-12 chain and/or improving the penetration of the peptide variant into the cell membrane. In one embodiment, the lipid- and/or sugar-conjugated peptide variants comprise D-amino acids, thereby increasing resistance to protease degradation. In one embodiment, a protease resistant peptide variant is useful clinically for inhibiting TREM-mediated cell activation in myeloid cell-mediated disorders.

In some embodiments, conjugated peptide variants are synthesized using the standard procedures (Amon et al. Biochim Biophys Acta 2006; 1763:879-88; Whittaker et al. Pept Res 1993; 6:125-8; In: Chemistry of Peptide Synthesis, N. Leo Benoiton (ed.), CRC, 2005; Gerber et al. Faseb J 2005; 19:1190-2; Kliger et al. J Biol Chem 1997; 272:13496-505; Merrifield et al. Biochemistry 1982; 21:5020-31).

In one embodiment, the rational design method comprises inserting at least one polyarginine and/or polylysine sequence into a TREM-1 transmembrane sequence, thereby increasing binding to a transmembrane domain of an DAP-12 chain and/or improving the penetration of the peptide variant into the cell membrane. Other modifications of the peptides contemplated herein include, but are not limited to, modifications to side chains, incorporation of unnatural amino acids and/or their derivatives during peptide synthesis and the use of crosslinkers and other methods which impose conformational constraints on the peptides. It may also be possible to add various groups to the peptide of the present invention to confer advantages such as increased potency or extended half life in vivo without substantially decreasing the biological activity of the peptide. It is intended that such modifications to the peptide of the present invention which do not result in a decrease in biological activity are within the scope of the present invention.

Any combination of the above embodiments may be used together in order to increase effectiveness of the peptide variants to inhibit the function of a TREM-1/DAP-12 receptor complex. The most effective inhibitory peptides and derivatives thereof may be identified by typical screening assay procedures for evaluation of inhibition of TREM-mediated cell activation and function (Ford J. W. & McVicar D. W. Curr Opin Immunol 2009; 21, 38-46; Klesney-Tait et al. Nat Immunol 2006; 7:1266-73).

5. Peptide-Based Inhibitors

Although it is not necessary to understand the mechanism of an invention, it is believed that inhibition of a TREM receptor (i.e., for example, TREM-1/DAP-12 receptor complex) signaling can be achieved by binding of a peptide-based inhibitor to the transmembrane (TM) domain of the DAP-12 chain, thus substituting the TREM-1 subunit and abolishing the interaction between the TM domains of the TREM-1 and DAP-12 chains. One possible result is the inhibition of TREM-1-mediated transmembrane signaling because ligand binding to the extracellular domain of a TREM-1 ligand recognition subunit does not lead to DAP-12 signaling subunit clustering (i.e., for example, oligomerization). It is further believed that this clustering induces the phosphorylation of tyrosine residues in the intracellular DAP-12 domain and initiates downstream signaling.

The TM domains of TREM-1 and DAP-12 subunits comprise hydrophobic sequences that may adopt a stable alpha-helical structure within a cell plasma membrane lipid bilayer. It is hypothesized that electrostatic interactions between these TM domains maintain the integrity of the TREM-1/DAP-12 receptor signaling complex and are provided by the interaction between positively charged Lys residue of the TREM-1 TM domain and two negatively charged Asp residues of the TM domains of the DAP-12 dimer.

It might be suggested that, theoretically, the simplest and the most selective and effective peptide inhibitor would be a synthetic peptide corresponding to the TM domain of TREM-1 subunit. However, as several embodiments of the present invention contemplate, peptide inhibitor sequence, alone, is not the only relevant consideration. In one embodiment, a peptide inhibitor targeted to the transmembrane interactions should be optimized for cell membrane binding. In one embodiment, a peptide inhibitor should be optimized for membrane insertion, thereby attaining a close spatial proximity and/or proper orientation to an interacting partner (i.e., for example, a TM domain of a DAP-12 dimer). In one embodiment, a peptide inhibitor should be optimized for binding effectiveness to an interacting partner.

Although it is not necessary to understand the mechanism of an invention, it is believed that a peptide inhibitor comprising the wild type TM domain of TREM-1 is not optimized for each of the above three factors. Other embodiments, however, are contemplated by the present invention by using extracellularly administered synthetic peptides which are optimized for at least one of the above three considerations. Thus, the inhibition of cell activation by the TREM-1 core peptide can be significantly improved in terms of efficiency by rational design of the peptide-based inhibitors. For example, the inhibition activity the T cell antigen receptor core peptide has been reported to increase from 30 to 80% by lipidation of the relevant peptide inhibitors.

In summary, the present invention contemplates optimizing the effectiveness and selectivity of peptide inhibitors for TREM-1/DAP-12-mediated signaling, by adhering to at least one of these guidelines:

1) ability to effectively bind to the cell plasma membrane and insert into the membrane (i.e., for example, increasing hydrophobicity);

2) ability to adopt helical conformation upon membrane binding and insertion (i.e., for example, increasing intrinsic helicity);

3) ability to selectively and effectively bind to the TM domain of the DAP-12 subunit, thus effectively competing with the TREM-1 subunit for the binding to the DAP-12 subunit (i.e., for example, by increasing stable alpha-helixes).

The following guidelines were used to develop a method of rational designing of the peptides in order to increase effectiveness of the peptides in inhibition of function of the TREM-1/DAP-12 receptor complex.

5.1. Hydrophobicity

The hydrophobicity (or lipophilicity) of peptides and peptide analogues may be increased by i) inserting hydrophobic regions; ii) improving the ability of a peptide-based inhibitors to bind the membrane; and/or iii) improving the ability of a peptide-based inhibitor to insert into a membrane. In one embodiment, hydrophobic regions may be inserted into a peptide inhibitor sequence by using lipophilic groups including, but not limited to, myristoylate-, 1-amino-glucose succinate, 2-aminododecanoate, or Gly-Tris-palmitate, -dipalmitate or -tripalmitate, coupled to the N- and/or C-termini of a peptide. In one embodiment, the membrane binding/insertion ability of a peptide inhibitor may be improved by using highly positively charged poly-Lys or poly-Arg sequences coupled to an N- and/or C-terminus. A general formula summarizing many suggested inhibitory peptides and/or compositions is presented that incorporates both approaches that are expected to increase the effectiveness of the peptides to inhibit the function of a TREM-1/DAP-12 receptor complex. See, FIG. 8.

Lipid-binding activity of the test peptide-based inhibitors can be predicted using ProtParam™ software (us.expasy.org/tools/protparam.html) and experimentally evaluated by different techniques such as, for example, surface plasmon resonance (SPR) or sucrose-loaded vesicle binding assay. Based on the obtained results, a peptide-based inhibitor with optimal membrane-binding activity can be chosen. For example, "Grand Average Of Hydropathy" (GRAVY) scores for peptides can be obtained using ProtParam™, in which a score>–0.4 (=mean score for cytosolic proteins) indicates the probability for membrane association (i.e., for example, the higher the score, the greater the probability for membrane association).

5.2. Helicity

As discussed above, the primary sequence of the parent inhibitory peptide, the TREM-1 core peptide, can be modified to improve the ability of various peptide-based inhibitors contemplated herein to adopt helical conformation upon membrane binding and insertion. See, FIG. 8. Overall protein folding may be specified by hydrophobic-polar residue patterning, whereas the bundle oligomerization state, detailed main-chain conformation, and interior side-chain rotamers may be engineered by computational enumerations of packing in alternate backbone structures. Main-chain flexibility is incorporated through an algebraic parameterization of the backbone (Harbury et al. Science 1998; 282:1462-7).

Peptide helicity of the designed primary sequences of various peptide-based inhibitors contemplated herein can be first evaluated computationally using secondary structure prediction programs. (i.e., for example, Expasy Proteomics Tools; http://expasy.org/tools). The most promising inhibitors can be measured experimentally for intrinsic and/or induced helicity using circular dichroism (CD) spectroscopy. CD spectroscopy is used to analyze the secondary structure of a protein and/or peptide. Specifically, CD spectroscopy measures differences in the absorption of left-handed polarized light versus right-handed polarized light which arise due to structural asymmetry. The absence of regular structure results in zero CD intensity, while an ordered structure results in a spectrum which can contain both positive and negative signals. alpha-helix, beta-sheet, and random coil structures each give rise to a characteristic shape and magnitude of CD spectrum. The approximate fraction of each secondary structure type that is present in any peptide or protein can thus be determined by analyzing its far-UV CD spectrum as a sum of fractional multiples of such reference spectra for each structural type. Like all spectroscopic techniques, the CD signal reflects an average of the entire molecular population. Thus, while CD can determine that a peptide or protein contains about 50% alpha-helix, it cannot determine which specific residues are involved in the alpha-helical portion. Based on the obtained results, a peptide-based inhibitor optimized with the predicted and/or observed, intrinsic and/or induced optimal helicity can be chosen.

Alternatively, secondary structure prediction programs (for example, http://expasy.org/tools/) may be used to accurately predict the peptide helicity based on primary sequence of the computationally designed peptide-based inhibitors. A few of the available programs include, but are not limited to: a) AGADIR—An algorithm to predict the helical content of peptides; b) APSSP—Advanced Protein Secondary Structure Prediction Server; c) GOR—Garnier et al. Methods Enzymol 1996; 266:540-53; d) HNN—Hierarchical Neural Network method (Guermeur et al. Bioinformatics 1999; 15:413-21) e) Jpred—A consensus method for protein secondary structure prediction at University of Dundee; f) JUFO—Protein secondary structure prediction from sequence (neural network); g) nnPredict—University of California at San Francisco (UCSF); h) Porter—University College Dublin; i) PredictProtein—PHDsec, PHDacc, PHDhtm, PHDtopology, PHDthreader, MaxHom, EvalSec from Columbia University; j) Prof—Cascaded Multiple Classifiers for Secondary Structure Prediction; k) PSA—BioMolecular Engineering Research Center (BMERC)/Boston; l) PSIpred—Various protein structure prediction methods at Brunel University; m) SOPMA—Geourjon and Deleage, 1995; n) Sspro—Secondary structure prediction using bidirectional recurrent neural networks at University of California; and o) DLP—Domain linker prediction at RIKEN.

5.3. alpha-Helix Stability

Although it is not necessary to understand the mechanism of an invention, it is believed that the TM domains of the TREM-1 and the DAP-12 subunits represent stable alpha-helixes and, thus, the interactions can be presented using helix-wheel diagrams. See, FIGS. 5, 6, and 7. As described in (US Pat Appl 20090075899) and incorporated herein by reference in its entirety, these diagrams are based on the primary peptide/protein sequence and can be created using commercially and publicly available programs (i.e., including, but not limited to, Antheprot v.6.0; or Helical Wheel Custom Images and Interactive Java Applets;). These diagrams can be used for evaluation of close proximity and/or proper orientation of positively charged amino acid residue(s) of the peptide or peptide analogue of interest towards an interacting partner (i.e., for example, negatively charged TM residues of a DAP-12 dimer).

Figure 5:
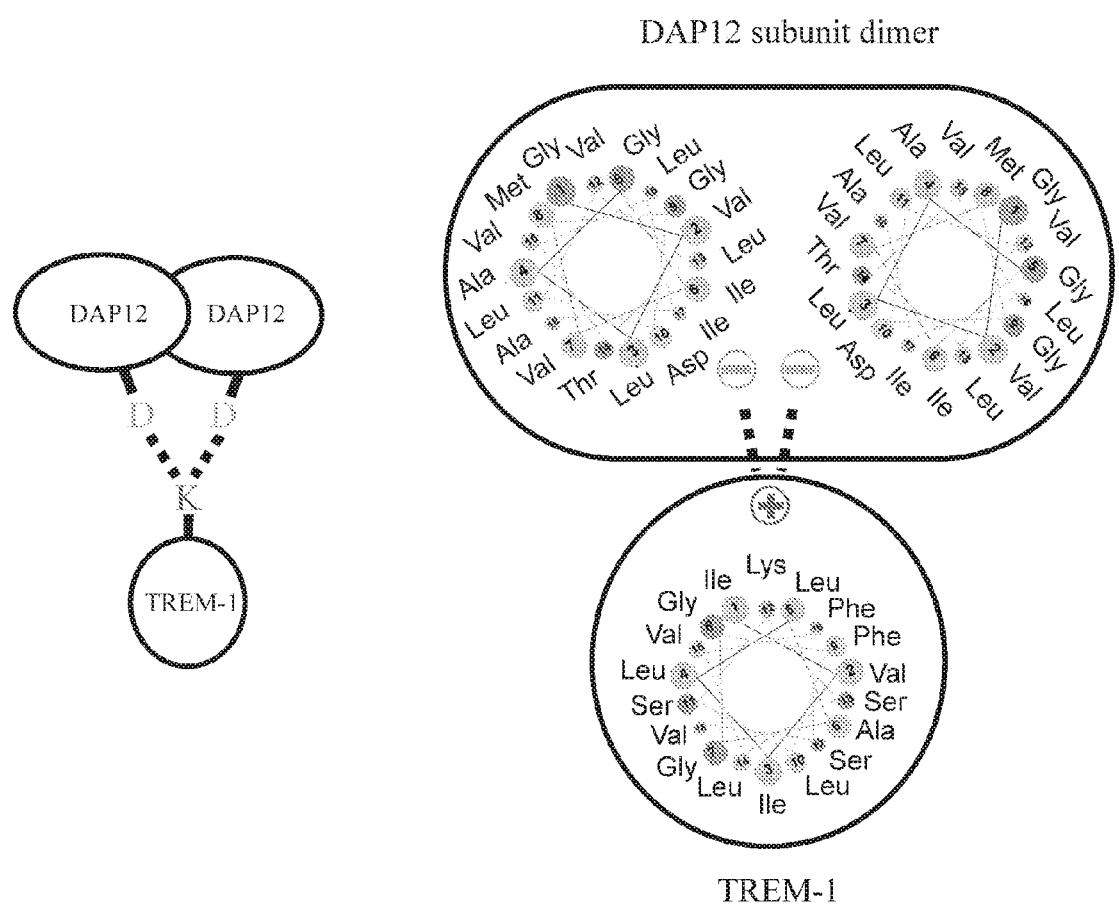
FIG. 5 illustrates one embodiment of normal interactions between TREM-1 and a DAP-12 subunit dimer to form a functional TREM-1/DAP-12 receptor complex.
Figure 6:
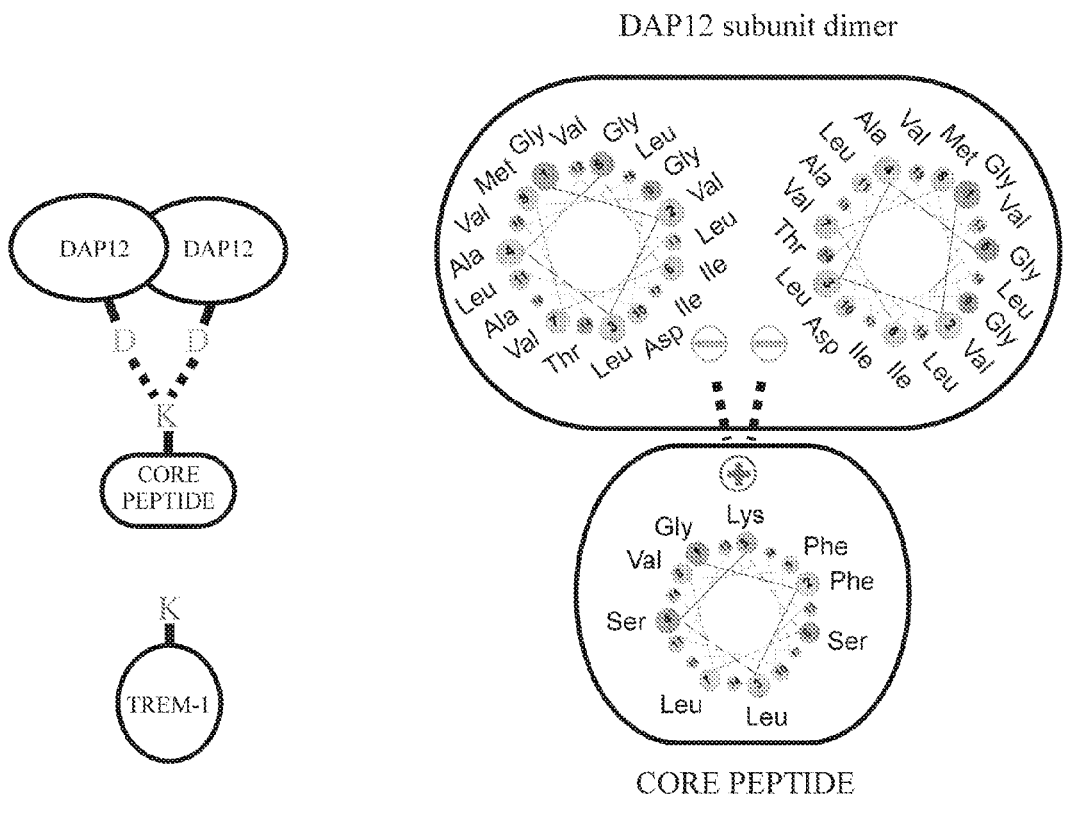
FIG. 6 illustrates one embodiment of disrupted interactions between TREM-1 and DAP-12 resulting in a non-functional TREM-1/DAP-12 receptor complex.
Figure 6:
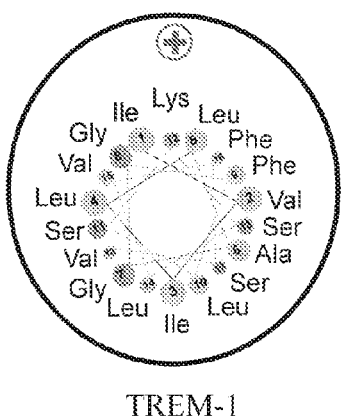
Figure 7:
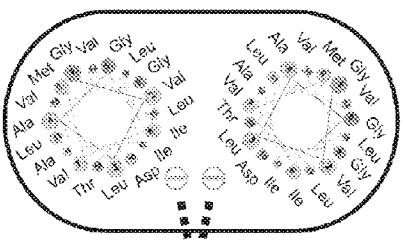
FIG. 7 illustrates one embodiment of modulation of binding of the TREM-1 Core and/or Extended peptides to the transmembrane domain of the DAP-12 subunit dimer.
Figure 7:
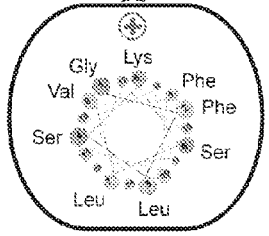
Figure 7:
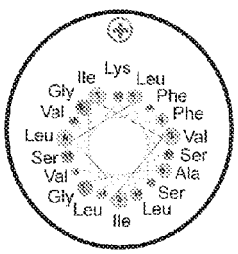
Figure 7:
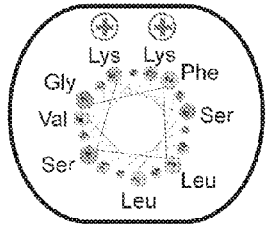
Figure 7:
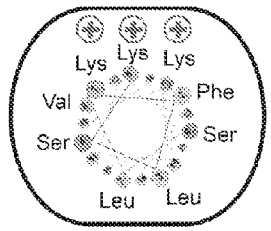
Figure 7:
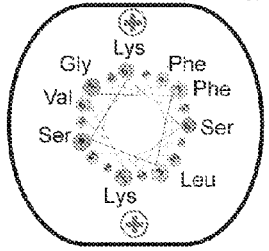
Figure 7:
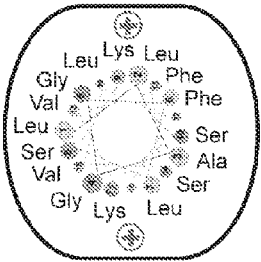

As shown in the FIG. 5, the electrostatic interaction between the TREM-1 TM positively charged Lys (K, blue) and the negatively charged aspartic acid pair (D, pink) in the DAP-12 dimer stabilize the association of these respective subunits, thereby playing a role in ligand-induced TREM-1-mediated cell activation and response. Some embodiments of peptide-based inhibitors contemplated by the present invention aim to interrupt this interaction and replace the TREM-1 subunit of the TREM-1/DAP-12 receptor complex. In one embodiment, peptide-based inhibitors can be computationally designed to increase their competitiveness with the TREM-1 subunit. In one embodiment, competitiveness may be increased by using a conservative amino acid substitution of lysine for arginine. In another embodiment, competitiveness may be hincreased by inserting a positively charged amino acid residue (i.e., for example, arginine and/or lysine). In one embodiment, the insertion and/or substitution is located within an alpha-helix of the peptide-based inhibitors (i.e., for example, a TREM-1 core or Extended Peptides; FIG. 7), thereby increasing the binding activity to transmembrane domains of the DAP-12 signaling subunit dimer and enhancing the effectiveness of the peptides to inhibit the function of the a TREM-1/DAP-12 receptor complex.

6. Peptide-Based Inhibitor Sequence Listings

A list of the sequences of the peptides and peptide analogues shown below includes, but is not limited to, peptide-based inhibitors predicted to be effective in inhibiting the TREM-1/DAP-12 signaling mechanism. See Table 2.

Accordingly, it is intended that the present invention includes within its scope peptides which include additional amino acids to the "core" sequence of the peptide of the present invention and which affect the transmembrane interactions between the TREM-1 subunit and DAP-12 dimer.

TABLE 2

Exemplary Peptide-Based TREM-1/DAP-12 Complex Inhibitor Sequences

| ## | $R_1{}^a$ | Sequence (the "core" sequence of the peptide of the present invention is underlined) | $R_2{}^b$ |
|---|---|---|---|
| 1 | — | IVILLAGG<u>GFLSKSLVF</u>SVLFA (parent) (TREM-1 TM peptide) | — |
| 2 | — | <u>GFLSKSLVF</u> (TREM-1 TM core peptide) | — |
| 3 | — | IVILLAGGFLSKSLVFSVLFA | + |
| 4 | LA | IVILLAGGFLSKSLVFSVLFA | — |
| 5 | Myr | GSVILLAGGFLSKSLVFSVLFA | — |
| 6 | LA | IVILLAGGFLSKSLVFSVLFA | + |
| 7 | — | KKILLAGGFLSKSLVFSVLFAKR | — |
| 8 | — | KKILLAGGFLSKSLVFSVLFAKR | + |
| 9 | — | (IVILLAGGFLSKSLVFSVLFA)$_2{}^c$ | — |
| 10 | — | IVILLACGFLSKSLVFSVLFA | — |
| 11 | — | (IVILLAC*GFLSKSLVFSVLFA)$_2{}^d$ | — |
| 12 | — | IVILLAGGFLSKSLVRSVLFA | — |
| 13 | — | IVILLAGGFLSKSLVRSVLFA | + |
| 14 | LA | IVILLAGGFLSKSLVRSVLFA | — |
| 15 | Myr | GSILLAGGFLSKSLVRSVLFA | — |
| 16 | — | KKILLAGGFLSKSLVRSVLFAKR | — |
| 17 | LA | KKILLAGGFLSKSLVRSVLFAKR | — |

TABLE 2-continued

Exemplary Peptide-Based TREM-1/DAP-12 Complex Inhibitor Sequences

| ## | $R_1{}^a$ | Sequence (the "core" sequence of the peptide of the present invention is underlined) | $R_2{}^b$ |
|---|---|---|---|
| 18 | — | KKILLAGGFLSKSLVRSVLFAKR | + |
| 19 | — | (IVILLAGGFLSKSLVRSVLFA)$_2$ | — |
| 20 | — | IVILLACGFLSKSLVRSVLFA | — |
| 21 | — | (IVILLAC*GFLSKSLVRSVLFA)$_2$ | — |
| 22 | — | IVILLAGRFLSKSLVRSVLFA | — |
| 23 | LA | IVILLAGRFLSKSLVRSVLFA | — |
| 24 | — | IVILLAGRFLSKSLVRSVLFA | + |
| 25 | — | KKILLAGRFLSKSLVRSVLFAKR | — |
| 26 | LA | KKILLAGRFLSKSLVRSVLFAKR | — |
| 27 | — | KKILLAGRFLSKSLVRSVLFAKR | + |
| 28 | — | (IVILLAGRFLSKSLVRSVLFA)$_2$ | — |
| 29 | — | IVILLACRFLSKSLVRSVLFA | — |
| 30 | — | (IVILLAC*RFLSKSLVRSVLFA)$_2$ | — |
| 31 | — | GFLSKSLVF | — |
| 32 | LA | GFLSKSLVF | — |
| 33 | — | GFLSKSLVF | + |
| 34 | — | (GFLSKSLVF)$_2$ | — |
| 35 | — | ACGFLSKSLVF | — |
| 36 | — | (AC*GFLSKSLVF)$_2$ | — |
| 37 | — | GLLSKSLVF | — |
| 38 | LA | GLLSKSLVF | — |
| 39 | — | GLLSKSLVF | + |
| 40 | — | (GLLSKSLVF)$_2$ | — |
| 41 | — | ACGLLSKSLVF | — |
| 42 | — | (AC*GLLSKSLVF)$_2$ | — |
| 43 | — | GLLSKTLVF | — |
| 44 | LA | GLLSKTLVF | — |
| 45 | — | GLLSKTLVF | + |
| 46 | — | (GLLSKTLVF)$_2$ | — |
| 47 | — | ACGLLSKTLVF | — |
| 48 | — | (AC*GLLSKTLVF)$_2$ | — |
| 49 | — | GFLSKSLVR | — |
| 50 | LA | GFLSKSLVR | — |
| 51 | — | GFLSKSLVR | + |
| 52 | — | (GFLSKSLVR)$_2$ | — |
| 53 | — | ACGFLSKSLVR | — |
| 54 | — | (AC*GFLSKSLVR)$_2$ | — |

TABLE 2-continued

Exemplary Peptide-Based TREM-1/DAP-12 Complex Inhibitor Sequences

| ## | $R_1{}^a$ | Sequence (the "core" sequence of the peptide of the present invention is underlined) | $R_2{}^b$ |
|---|---|---|---|
| 55 | — | KFLSKSLVR | — |
| 56 | LA | KFLSKSLVR | — |
| 57 | — | KFLSKSLVR | + |
| 58 | — | (KFLSKSLVR)$_2$ | — |
| 59 | — | ACKFLSKSLVR | — |
| 60 | — | (AC*RFLSKSLVR)$_2$ | — |
| 61 | — | VTISVICGLLSKSLVFIILFI | — |
| 62 | — | (VTISVICGLLSKSLVFIILFI)$_2$ | — |
| 63 | — | (VTISVIC*GLLSKSLVFIILFI)$_2$ | — |
| 64 | — | IIIPAACGLLSKTLVFIGLFA | — |
| 65 | — | (IIIPAACGLLSKTLVFIGLFA)$_2$ | — |
| 66 | — | (IIIPAAC*GLLSKTLVFIGLFA)$_2$ | — |
| 67 | — | ILPAVCGLLSKSLVFIVLFVV | — |
| 68 | — | ILPAVCKLLSKSLVFIVLFVV | — |
| 69 | — | (ILPAVCGLLSKSLVFIVLFVV)$_2$ | — |
| 70 | — | (ILPAVC*GLLSKSLVFIVLFVV)$_2$ | — |

$^a$N-terminal group: LA, lipoamino acid, 2-aminododecanoate; Myr, myristoylate.
$^b$C-terminal group: Gly-Tris-tripalmitate.
cCyclic peptide.
$^d$Disulfide-linked dimer (or disulfide-linked cyclic dimer).
* Cys involved in disulfide bond formation.
Abbreviations: TM, transmembrane 7. Peptide Variant Consensus Sequences Based upon the specific sequences contemplated in Table 2, the following consensus sequences may be constructed:

SEQ ID NO: 1: G-$X_1$-$X_2$-L-S-$X_3$-$X_4$-L-V-$X_5$-$X_6$-$X_7$-$X_8$-$X_9$-$X_{10}$, wherein $X_1$ consists of G, C or is selected from the group consisting of R, K or H; $X_2$ is selected from the group consisting of L, F or I; $X_3$ is selected from the group consisting of R, K or H; $X_4$ is selected from the group consisting of S or T; $X_5$ consists of F or is selected from the group consisting of R, K or H; $X_6$ consists of S, I, L or nothing; $X_7$ consists of V, I, L, G or nothing; and $X_8$, $X_9$, and $X_{10}$ consist of L, F, A or nothing.

SEQ ID NO: 2: $X_1$-$X_2$-$X_3$-G-F-L-S-K-S-L-V-R-V-$X_4$-$X_5$, wherein $X_1$ consists of G, C or nothing; and $X_2$, $X_3$, $X_4$, and $X_5$ consist of K, R, or nothing.

SEQ ID NO: 3: $X_1$-$X_2$-$X_3$-L-$X_4$-$X_5$-$X_6$-$X_7$-G-$X_8$-L-S-K-$X_9$-L-V-F-$X_{10}$-$X_{11}$-L-F-$X_{12}$-$X_{13}$-$X_{14}$-$X_{15}$, wherein $X_1$ consists of G or nothing; and $X_2$, $X_3$, $X_{14}$, and $X_{15}$ consist of K, R, or nothing; $X_4$, $X_5$, $X_6$, and $X_7$ consist of P, A, V, C, L, I, S, G or nothing; $X_8$ consists of F, L or I; $X_9$ consists of S or T; $X_{10}$, $X_{11}$, $X_{12}$, and $X_{13}$ consist of S, I, L, G, V, A, or nothing.

8. Therapeutic Applications of TREM-1/DAP-12 Peptide Inhibitors

The invention further provides clinically therapeutic methods of intervening and modulating TREM-1 function comprising using an agent selected from the group of agents or compositions of the present invention that block/inhibit/prevent/disrupt interactions between the TREM-1 chain and the homodimeric DAP-12 subunit of the TREM-1/DAP-12 complex.

High-throughput screening methods that can be used for screening and optimizing the effective TREM-1 peptide inhibitors of the present invention that block/inhibit/prevent/disrupt interactions between the TREM-1 chain and the homodimeric DAP-12 subunit of the TREM-1/DAP-12 receptor complex are described in US Pat Appl 20090075899 and incorporated herein by reference in its entirety. See also FIGS. 2, 4, 9, 10, and 11.

Various therapeutic applications of TREM-1 inhibitors are described in (Bouchon et al. J Immunol 2000; 164:4991-5; Ford J. W. & McVicar D. W. Curr Opin Immunol 2009; 21, 38-46; Bouchon et al. Nature 2001; 410:1103-7; Gibot S. Crit Care 2005; 9:485-9; Gibot et al. J Exp Med 2004; 200:1419-26; Gibot et al. Shock 2009; 32:633-7; Gibot et al. Crit Care Med 2008; 36:504-10; Klesney-Tait et al. Nat Immunol 2006; 7:1266-73; Murakami et al. Arthritis Rheum 2009; 60:1615-23; Sharif O. & Knapp S. Immunobiology 2008; 213:701-13; US Pat Appls 20080247955, 20060246082, 20090081199, and 20030165875; U.S. Pat. No. 6,420,526; Ling et al. Chinese Med J 2010; 123:1561-5; Ho et al. Am J Respir Crit Care Med 2008; 177:763-70) and incorporated herein by reference in their entirety.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

EXAMPLES

The invention now being generally described, it will be more readily understood by reference to the following examples, which are included merely for purposes of illustration of certain aspects and embodiments of the present invention, and are not intended to limit the invention.

The following non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the invention and are not intended to limit the scope of what the inventor regard as his invention. Efforts have been made to ensure accuracy with respect to numbers (e.g., amounts, temperature, etc.) but some errors and deviations should be accounted for. Unless indicated otherwise, parts are parts by weight, temperature is in ° C., or is at ambient temperature, and pressure is at or near atmospheric.

Example 1

Synthesis of Peptides

This example demonstrates one embodiment of a synthesized TREM-1 transmembrane peptide.

The first step is to synthesize the short hydrophobic peptide corresponding to a portion of a TREM-1 transmembrane domain sequence. Although it is not necessary to understand the mechanism of an invention, it is believed that this peptide affects the TREM-1/DAP-12 receptor complex assembly and may interact with the DAP-12 homodimer in a competitive fashion.

The synthesis of peptides may involve the use of protecting groups. Peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

In one embodiment, the amino acid sequence of a competitive peptide comprises $NH_2$-Gly-Phe-Leu-Ser-Lys-Ser-Leu-Val-Phe-OH (i.e., GFLSKSLVF), hereafter referred to as "core peptide" or "CP". In another embodiment, the amino acid sequence of a competitive peptide comprises $NH_2$-Gly-Phe-Leu-Ser-Ala-Ser-Leu-Val-Phe-OH (i.e., GFLSASLVF) wherein, $Lys^5$ of CP substituted with $Ala^5$, hereafter referred to as "CP-A".

Although it is not necessary to understand the mechanism of an invention, it is believed that the positively charged $Lys_5$ in the CP transmembrane domain of TREM-1 forms a salt bridge to an aspartic acid residue in the transmembrane domain of the DAP-12 chain. Thus, CP-A may be considered as "control peptide" because of the $Lys^5$ substitution. In one embodiment, a scrambled peptide containing the same amino acids as "core peptide" but in a totally different sequence order (e.g., LFGFLVSSK) can be similarly synthesized and used as control peptide.

Unprotected peptides can be purchased from specialized companies (i.e., Sigma-Genosys, Woodlands, Tex., USA) with greater than 95% purity as assessed by HPLC. Peptide molecular mass can be checked by matrix-assisted laser desorption ionization mass spectrometry.

Example 2

Solubility

This example demonstrates that the hydrophobic properties of CP peptides and other peptides and compositions of the present invention may be overcome without risking cell toxicity. This example further demonstrates that the hydrophobic properties of TREM-1 core peptides may be overcome without risking cell toxicity.

The CP and CP-A peptides can be hydrophobic and insoluble in aqueous solutions. A variety of solvents and carriers can be tested to improve their solubility. Solvents and/or carriers that improve solubility of CP and CP-A include, but are not limited to, ethanol, dimethylsulphoxide (DMSO), dimethyl formamide (DMF), and trifluoroacetic acid (TFA). When using DMSO as a solvent, the final concentration used in the cell function experiments may range from 0.063%-0.250%. Stock solutions of CP and CP-A can be prepared in DMSO and used at a 1:2000, 1:1000, or 1:400 dilution. In one embodiment, drug delivery systems (i.e., for example, lipid vesicles) can be used to increase solubility and bioavailability of CP and CP-A.

Example 3

Preparation of Small Unilamellar Vesicles (SUVs)

Model membranes composed of zwitterionic and anionic phospholipids and their mixtures in proportion similar to that found in vertebrate cell membranes can be produced as follows. Dimyristoyl-L-alpha-phosphatidylcholine (DMPC) and dimyristoyl-L-alpha-phosphatidyl-DL-glycerol (DMPG) are dissolved in dry chloroform and chloroform/methanol (2:1), respectively, to give 10 mg/ml solutions. These are evaporated under reduced pressure and the resulting lipid films are vacuum-dried overnight. Lipids are hydrated by resuspending in HEPES buffer for 60 min at 34° C. to give 0.5 mM concentration in respect of phospholipids. The solution is sonicated in an ultrasonic bath for 20 min. Eight cycles of freeze/thawing are followed by extrusion through polycarbonate filters, first 100 nm (21 times), then 50-nm pore diameters (21 times), using a Lipofast apparatus (Avestin, Ottawa, Canada) and the SUVs are used immediately.

Example 4

Surface Plasmon Resonance (SPR) Analysis of Lipid Binding Activity

SPR is carried out on a BIAcore™ 2000 instrument using Pioneer Sensor Chip L1 and HEPES (HBS-N, Biacore) as running buffer. The chip surface is cleaned with 40 mM octyl glycoside (30 mL, 10 mL/min) followed by running buffer (100 mL, 10 mL/min). Liposomes (small unilamellar vesicles, SUVs), made in accordance to Example 7, are injected (100 mL, 5 mL/min) giving a response of about 8000 RU. 10 mM NaOH (40 mL, 10 mL/min) removes any multilamellar vesicles from the surface that is followed by 10 mM glycine, pH 2.2 (10 mL, 10 mL/min), before injecting a TREM-1 peptide or peptide analogue inhibitor (100 mL, 5 mL/min). After peptide injection the dissociation stage is 1200 s. Regeneration of the sensor chip is achieved with 40 mM octyl glycoside (30 mL, 10 mL/min). All SPR experiments are run at 25° C. and all analyses are performed using BIAevaluation software (Biacore). For the comparative binding of a peptide and/or peptide analogue, a determination of percentage binding is expressed as a percentage of the wild-type peptide binding. The values are representative of three injections under identical conditions for each peptide. To study the effect of interaction time on the wild-type peptide binding, the "variable contact times" injection command is utilized on the Biacore™ 2000 instrument. This is achieved by switching additional flow cells into the flow path as the injection proceeds; thus the injections end at the same time.

Example 5

Preparation of Sucrose-Loaded Vesicles

This example describes the preparation of sucrose-loaded large unilamellar vesicles (LUVs) for use in a sucrose-loaded vesicle binding assay. The corresponding lipid, the zwitterionic lipid 1-palmitoyl-2-oleoyl-sn-glycero-3-phosphocholine (POPC) or the acidic lipid 1-palmitoyl-2-oleoyl-sn-glycero-3-phosphoglycerol (POPG), or lipid mixtures in $CHCl_3$ are evaporated under argon and then vacuum-dried for 3 h at 20° C. The dried lipid is resuspended in 176 mM sucrose and 1 mM MOPS at pH 7.0; the air is displaced with argon. LUVs are made after five freeze-thaw cycles by extruding multilamellar vesicles 10 times through a stack of two polycarbonate filters (100-nm pore diameter) in an Avanti mini-extruder (Avanti Polar Lipids, Alabaster, Ala.). The vesicle solution is diluted 5 times with 1 mM MOPS buffer, pH 7.0, containing 0.1 M KCl and osmotic to the internal sucrose buffer, and centrifuged at 100,000 g for 1 h at 25° C. using a table-top Beckman TL-100 ultracentrifuge equipped with a TLA-45 rotor. The supernatant is removed, and the lipid pellet is resuspended in the same buffer solution. The final concentration of the vesicle solution is determined using a phosphorous assay.

Example 6

Sucrose-Loaded Vesicle Binding Assay

In the membrane-binding assay, peptide or peptide analogue in a final concentration of 10 mM is mixed with the sucrose-loaded LUVs; [peptide]<<[lipid] so that the peptide does not bind a significant fraction of the lipid. After 15 min of equilibration at room temperature (20° C.), vesicle-bound peptide or peptide analogue is separated by centrifugation (for 1 h at 100,000 g and 25° C.). Ninety percent of the supernatant and pellet is evaluated for protein content using a fluorescamine assay. The percentage of the protein bound at a given lipid concentration is calculated and corrected for the 1-3% lipid that remains in the supernatant.

Example 7

Circular Dicroism Spectroscopy Analysis of a Peptide Secondary Structure

Far-UV CD spectra can be recorded on an Aviv 202 spectropolarimeter (AVIV Instruments, Lakewood, N.J.) with 0.01 mM peptide or peptide analogue in the absence or presence of SDS and/or lipids, or helicity inducers, such as TFE, in phosphate buffered saline buffer (PBS; 137 mM NaCl, 10 mM sodium phosphate, 2.7 mM KCl, pH 7.4) in 1.0 mm path-length cells. Data are collected at 25° C. every nanometer from 260 to 190 nm with 1.0 s averaging per point and a 1 nm bandwidth. The CD spectra of at least six scans are signal averaged, baseline corrected by subtracting an averaged buffer spectrum, and normalized to molar residue ellipticity.

Example 8

Protection of Mice from Death by Septic Shock with TREM-1 Peptide Variants

The experiment can be conducted analogously to that described in US Pat Appl 20060246082, which is incorporated herein by reference in its entirety.
In the experiments of this example, the peptides are administered in a volume of 200 ul. To assess the ability of TREM-1 transmembrane peptides to protect mice from LPS-induced endotoxaemia, the CP and CP-A peptides at various concentrations are administered 1 hour before a lethal dose of lipopolysaccharide (LPS). Lethality is monitored over time and compared with animals that have received control injections of vehicle alone.

In order to investigate whether treatment with TREM-1 TM peptide variants can be delayed until after the administration of LPS, the peptides are injected at various time points after LPS injection. The peptides can be further investigated for their ability to protect against septic shock in another widely used experimental model of sepsis, the "CLP" model (Cecal Ligation and Puncture).

Example 9

Studies on the Modulation of the Inflammatory Response in Murine Sepsis by TREM-1 Peptide Variants The experiments can be conducted analogously to that described in US Pat Appl 20060246082, which is incorporated herein by reference in its entirety.
Methods
Preparation of Monocytes from Peripheral Blood Ten mL of peripheral blood samples are collected on EDTA-K from healthy volunteer donors. After dilution in RPMI (Life Technologies, Grand Island, N.Y.), blood is centrifuged for 30 min at room temperature over a Ficoll gradient (Amersham Pharmacia, Uppsala, Sweden) to isolate PBMC. The cells recovered above the gradient are washed and counted. In order to deplete the suspensions of lymphocytes, cells are then plated in 24-well flat-bottom tissue culture plates (Corning, Corning, N.Y.) at a concentration of $5 \times 10^6$/mL and allowed to adhere during 2 hours at 37° C. The resulting lymphocyte suspension is discarded and the adhering monocytic cells are maintained in a 5% $CO_2$ incubator at 37° C. in complete medium (RPMI 1640, 0.1 mM sodium pyruvate, 2 mM Penicillin, 50 ug/mL Streptomycin; Life Technologies) supplemented with 10% FCS (Invitrogen, Cergy, France).
In Vitro Stimulation of Monocytes For activation, monocytes are cultured in the presence of *E. coli* LPS (O111:B4, 1 ug/mL, Sigma-Aldrich, La Verpilliere, France). Cell viability is assessed by trypan blue exclusion and by measuring lactate dehydrogenase release. In some experiments, this stimulus is given in combination with TNF-alpha (5 to 100 ng/mL, R&D Systems, Lille, France), IL-1beta (5 to 100 ng/mL, R&D Systems), rIFN-gamma (up to 100 U/mL, R&D Systems), rIL-10 (500 U/ml, R&D Systems) or up to 100 ng/mL of CP or CP-A.

In order to activate monocytes through TREM-1, an anti-TREM-1 agonist monoclonal antibody (R&D Systems) is added as follows: flat-bottom plates are precoated with 10 ug/mL anti-TREM-1 per well. After thorough washing in phosphate buffered saline (PBS), the monocyte suspensions are added at a similar concentration as above. Some experiments are performed in the presence of protease inhibitors (PMSF and Protease Cocktail Inhibitor; Invitrogen). Cell-free supernatants are assayed for the production of TNF-alpha and IL-1beta by ELISA according to the recommendations of the manufacturer (BD Biosciences, San Diego, USA). To address the effect of CP on NF-κB activity in monocytes, an ELISA-based assay is performed (BD Mercury Transfactor Kit, BD Biosciences). Monocytes are cultured for 24 hours in the presence of *E. coli* LPS (O111:B4, 1 ug/mL), and/or an agonist anti-TREM-1 monoclonal antibody (10 ug/mL), with or without TREM-1 CP or control peptide added at various concentrations. Whole-cell extracts are then prepared and levels of NF-κB p50 and p65 are determined according to the recommendations of the manufacturer. All experiments are performed in triplicate.

Identification and Quantitation of sTREM-1 Release

Primary monocytes suspensions are cultured as described above. The cells are treated with *E. coli* LPS (O111:B4, 1 ug/mL) for 24 hours at 37° C. Cell-conditioned medium is submitted to Western-blotting using an anti-TREM-1 monoclonal antibody (R&D Systems) in order to confirm the presence of 27 kDa material recognized by anti-TREM-1. Soluble TREM-1 levels are measured by assessing the optical intensity of bands on immunodots by means of a reflectance scanner and the Quantity One Quantitation Software (Bio-Rad, Cergy, France). Soluble TREM-1 concentration from each sample is determined by comparing the optical densities of the samples with reference to standard curves generated with purified TREM-1. All measurements are performed in triplicate. The sensitivity of this technique allows the detection of sTREM-1 levels as low as 5 ug/mL.

CLP Polymicrobial Sepsis Model

Male Balb/C mice (7 to 9 weeks, 20 to 23 g) are anaesthetized by i.p. administration of ketamine and xylazine in 0.2 mL sterile pyrogen-free saline. The caecum is exposed through a 1.0 cm abdominal midline incision and subjected to a ligation of the distal half followed by two punctures with a G21 needle. A small amount of stool is expelled from the punctures to ensure patency. The caecum is replaced into the peritoneal cavity and the abdominal incision closes in two layers. After surgery all mice are injected s.c. with 0.5 ml of physiologic saline solution for fluid resuscitation and s.c. every 12 h with 1.25 mg (i.e. 50 ug/g) of imipenem. The animals are randomly grouped and treated with normal saline (n=14), control peptide (n=14; 100 ug) or TREM-1 CP (100 ug) in a single injection at H0 (n=18), H+4 (n=18) or H+24 (n=18). The last group of mice (n=18) is treated with repeated injections of CP (100 ug) at H+4, H+8 and H+24. All treatments are diluted into 500 ul of normal saline and administered i.p. To determine the effect of various doses of CP, mice (n=15 per group) are treated with a single injection of normal saline or 10 ug, 20 ug, 50 ug, 100 ug or 200 ug of CP at H0 after the CLP and monitored for survival. Five additional animals per group are killed under anaesthesia 24 hours after CLP for the determination of bacterial count and cytokines levels. Peritoneal lavage fluid is obtained using 2 mL RPMI 1640 (Life Technologies) and blood is collected by cardiac puncture. Concentrations of TNF-alpha and IL-1beta in the serum are determined by ELISA (BD Biosciences). For the assessment of bacterial counts, blood and peritoneal lavage fluid are plated in serial log dilutions on tryptic soy supplemented with 5% sheep blood agar plates. After plating, tryptic soy agar plates were incubated at 37° C. aerobically for 24 hours, and anaerobically for 48 hours. Results are expressed as CFU per mL of blood and CFU per mouse for the peritoneal lavage.

Statistical Analyses

The protection against LPS lethality by CP is assessed by comparison of survival curves using the Log-Rank test. All statistical analyses are completed with Statview software (Abacus Concepts, Berkeley Calif.).

Example 10

Haemodynamic Studies in Septic Rats Treated with TREM-1 Peptide Variants

The role of TREM-1 peptides in further models of septic shock, is investigated by performing LPS- and CLP-induced endotoxinemia experiments in rats. The experiments can be conducted analogously to that described in US Pat Appl 20060246082, which is incorporated herein by reference in its entirety.

Materials and Methods

LPS-Induced Endotoxinemia

Animals are randomly grouped (n=10-20) and treated with *Escherichia coli* LPS (O111:B4, Sigma-Aldrich, Lyon, France) i.p. in combination with TREM-1 CP or CP-A at various concentrations.

CLP Polymicrobial Sepsis Model

This procedure has been described in details elsewhere (Mansart et al. Shock 2003; 19:38-44). Briefly, rats (n=6-10 per group) are anesthetized by i.p. administration of ketamine (150 mg/kg). The caecum is exposed through a 3.0-cm abdominal midline incision and subjected to a ligation of the distal half followed by two punctures with a G21 needle. A small amount of stool is expelled from the punctures to ensure potency. The caecum is replaced into the peritoneal cavity and the abdominal incision closed in two layers. After surgery, all rats are injected s.c. with 50 mL/kg of normal saline solution for fluid resuscitation. TREM-1 CP or CP-A peptides are then administered at various concentrations.

Haemodynamic Measurements in Rats

Immediately after LPS administration as well as 16 hours after CLP, arterial BP (systolic, diastolic, and mean), heart rate, abdominal aortic blood flow, and mesenteric blood flow are recorded using a procedure described elsewhere (Mansart et al. Shock 2003; 19:38-44). Briefly, the left carotid artery and the left jugular vein are cannulated with PE-50 tubing. Arterial BP is continuously monitored by a pressure transducer and an amplifier-recorder system (IOX EMKA Technologies, Paris, France). Perivascular probes (Transonic Systems, Ithaca, N.Y.) are wrapped up the upper abdominal aorta and mesenteric artery, allowed to monitor their respective flows by means of a flowmeter (Transonic Systems). After the last measurement ($4^{th}$ hour after LPS and $24^{th}$ hour after CLP), animals are sacrificed by an overdose of sodium thiopental i.v.

Biological Measurements

Blood is sequentially withdrawn from the left carotid artery. Arterial lactate concentrations and blood gases analyses are performed on an automatic blood gas analyser (ABL 735, Radiometer, Copenhagen, Denmark). Concentrations of TNF-alpha and IL-1beta in the plasma are determined by an ELISA test (Biosource, Nivelles, Belgium) according to the recommendations of the manufacturer. Plasmatic concentrations of nitrates/nitrites are measured using the Griess reaction (R&D Systems, Abingdon, UK).

Statistical Analyses

Between-group comparisons are performed using Student't tests. All statistical analyses are completed with Statview software (Abacus Concepts, Calif.).

Example 11

Effect of TREM-1 Peptide Variants on Production of Cytokines and Chemokines, Degranulation, and Expression of Cell Surface Activation Markers These assays (as described in US Pat Appl 20090081199, and incorporated herein by reference in its entirety) can be performed to demonstrate that the TREM-1 peptide variants are effective in inhibiting TREM-1-mediated cell activation.

Stimulation of TREM-1

To examine whether TREM-1 can trigger acute inflammatory responses, purified monocytes or neutrophils are stimulated for 24 h in 96-well flat-bottom plates coated with F(ab')$_2$ goat anti-mouse IgG (5 ug/ml) followed by either 21C7, 1F11 (anti-MHC class I), or 1B7.11 (anti-2,4,6 TNP) mAbs. Cells are plated at a concentration of 5×10$^4$ cells/well in the presence or absence of LPS (1 ug/ml). Supernatants are collected and tested for production of IL-6, IL-8, IL-10, IL-12p75, monocyte chemoattractant protein-1 (MCP-1), TNF-alpha, and myeloperoxidase (MPO) by ELISA (PharMingen, San Diego, Calif.). To measure the expression of cell surface markers, monocytes and neutrophils are stimulated as described above and, after 48 hours, are stained with PE- or FITC-conjugated anti-CD11b, anti-CD11c, anti-CD18, anti-CD29, anti-CD32, anti-CD40, anti-CD49d, anti-CD49e, anti-CD54, anti-CD80, anti-CD83, or anti-CD86 (all from Immunotech, Marseille, France) and analyzed by FACS. To demonstrate TREM-1 inhibitory activity of TREM-1 peptide variants, either a TREM-1 peptide variant (e.g., the TREM-1 CP peptide, GFLSKSLVF), or a sequence-scrambled control peptide (e.g., LFGFLVSSK), or a TREM-1 CP-A control peptide (GFLSASLVF) are added to cells at various concentrations before stimulation.

Measurement of Cytosolic Ca$^{2+}$ and Tyrosine-Phosphorylated Proteins

Determination of intracellular Ca$^{2+}$ mobilization can be done according to the previous reports (Nakajima et al. J Immunol 1999; 162:5-8). Briefly, monocytes or monocyte-derived DCs are loaded with Indo-1 AM dye (Sigma) for 30 min at 37° C., washed 3 times and resuspended in RPMI-10 mM HEPES/10% FCS. Cytoplasmic Ca$^{2+}$ levels are monitored in individual cells by measuring 405/525 spectral emission ratio of loaded Indo-1 dye by flow cytometry (Nakajima et al. J Immunol 1999; 162:5-8; Yamashita et al. J Immunol 1998; 161:4042-7). After obtaining the baseline for at least 30 seconds, for TREM-1 stimulation, anti-TREM-1 mAb or anti-MHC class I (isotype-matched control mAb) and a cross-linking Ab (goat anti-mouse IgG) are added to the monocytes, and analysis is allowed to continue. For TREM-2 stimulation, either 29E3$^{Biotin}$ (IgG1, kappa or Fab) or 21C7$^{Biotin}$ (IgG1, kappa or Fab) is added to a final concentration of 1 μg/ml and analysis is continued up to 512 sec. In some experiments, ExtraAvidine (Sigma) is added as cross-linker together with the biotinylated primary antibodies or antibody fragments. To demonstrate TREM-1 inhibitory activity of TREM-1 peptide variants, either a TREM-1 peptide variant (e.g., the TREM-1 CP peptide, GFLSKSLVF), or a sequence-scrambled control peptide (e.g., LFGFLVSSK), or a TREM-1 CP-A control peptide (GFLSASLVF) are added to cells at various concentrations before TREM-1 stimulation.

Determination of protein tyrosine phosphorylation, mitogen activated protein kinase activation, phospholipase C-gamma (PLC-gamma) phosphorylation, and immunoprecipitations can be performed as previously described (Dietrich et al. J Immunol 2000; 164:9-12). Briefly, monocytes are incubated at 37° C. with 27C1 mAb (anti-TREM-1) or control IgG1 (anti-MHC class I) mAbs in the presence of a cross-linking Ab for the indicated time periods. After stimulation, an aliquot of the cells is lysed and subjected to anti-phosphotyrosine blotting using PY-20 (Transduction Laboratories, Lexington, Ky.). Another aliquot of stimulated monocytes or monocyte-derived DCs is examined by Western blot analysis using anti-phospho-extracellular signal-regulated kinase ½ (P-ERK1/2) and anti-ERK1/2 mAbs. Tyrosine phosphorylated proteins are precipitated from the stimulated monocyte lysates and immunoblotted with anti-PLC-gamma or anti-Hck Abs. An anti-Hck blotting is performed as a loading control because phosphorylation of Hck is similar in both stimulated and unstimulated monocytes. To demonstrate TREM-1 inhibitory activity of TREM-1 peptide variants, either a TREM-1 peptide variant (e.g., the TREM-1 CP peptide, GFLSKSLVF), or a sequence-scrambled control peptide (e.g., LFGFLVSSK), or a TREM-1 CP-A control peptide (GFLSASLVF) are added to cells at various concentrations before stimulation.

Example 12

Attenuation of Intestinal Inflammation in Animal Models of Colitis with TREM-1 Peptide Variants In order to demonstrate that the TREM-1 peptide variants are effective in inhibiting TREM-1-mediated cell activation in animal models of colitis, the experiments can be conducted analogously to that described in Schenk et al. J Clin Invest 2007; 117:3097-106, which is incorporated herein by reference in its entirety.

Methods

Mice

C57BL/6 mice, purchased from Harlan, and C57BL/6 RAG2−/− mice, bred in a specific pathogen-free (SPF) animal facility, are used at 8-12 weeks of age. All experimental mice are kept in micro-isolator cages in laminar flows under SPF conditions.

Mouse Models of Colitis

For experiments involving the adoptive T cell transfer model, colitis is induced in C57BL/6 RAG2−/− mice by adoptive transfer of sorted CD4+ CD45RBhigh T cells. Briefly, CD4+ T cells are isolated from splenocytes from C57BL/6 mice, and after osmotic lysis of erythrocytes, CD4+ T cells are enriched by a negative MACS procedure for CD8alpha and B220 (purified, biotinylated, hybridoma supernatant) using avidin-labeled magnetic beads (Miltenyi Biotec). Subsequently, the CD4+ T cell-enriched fraction is stained and FACS sorted for CD4+ (RM4-5; BD Biosciences—Pharmingen), CD45RBhi (16A; BD Biosciences-Pharmingen), and CD25- (PC61; eBioscience) naive T cells. Each C57BL/6 RAG2−/− mouse is injected i.p. with 1×105 syngeneic CD4+CD45RBhighCD25− T cells. Colitic mice are sacrificed and analyzed on day 14 after adoptive transfer.

For experiments involving the dextran sodium sulfate (DSS) colitis model, C57BL/6 mice are given autoclaved tap water containing 3% DSS (DSS salt, reagent grade, mol wt: 36-50 kDa; MP Biomedicals) ad libitum over a 5-day period. The consumption of 3% DSS is measured. DSS is replaced thereafter by normal drinking water for another 4 days. Mice are euthanized and analyzed at the end of the 9-day experimental period.

TREM-1 Peptide Treatment

Upon colitis induction, either starting on day 0 or after onset of colitis on day 3 (as indicated), mice are treated with either a TREM-1 peptide variant (e.g., the TREM-1 CP peptide, GFLSKSLVF), or a sequence-scrambled control peptide (e.g., LFGFLVSSK), or a TREM-1 CP-A control peptide (GFLSASLVF), as previously described for septic shock models by Gibot and coworkers (Gibot S., et al. J Exp Med 2004; 200:1419-26). The peptides are chemically synthesized as described herein. Mice are treated once daily with 200 ug peptide, injected i.p. in 200 ul saline.

Colitis Scoring

At the end of the experiments, the colon length is measured from the end of the cecum to the anus. Fecal samples are tested for occult blood using hemo FEC (Roche) tests (score 0, negative test; 1, positive test and no rectal bleeding; 2, positive test together with visible rectal bleeding). The colon is divided into 2 parts. From each mouse, identical segments from the distal and proximal colon are taken for protein and RNA isolation and histology, and frozen tissue blocks are prepared for subsequent analysis. Histological scoring of paraffin-embedded H&E-stained colonic sections is performed in a blinded fashion independently by 2 pathologists. To assess the histopathological alterations in the distal colon, a scoring system is established using the following parameters: (a) mucin depletion/loss of goblet cells (score from 0 to 3); (b) crypt abscesses (score from 0 to 3); (c) epithelial erosion (score from 0 to 1); (d) hyperemia (score from 0 to 2); (e) cellular infiltration (score from 0 to 3); and (f) thickness of colonic mucosa (score from 1 to 3). These individual histology scores are added to obtain the final histopathology score for each colon (0, no alterations; 15, most severe signs of colitis).

RNA Isolation and RT-PCR

RNA is isolated from intestinal tissue samples preserved in RNAlater (QIAGEN), using the RNAeasy Mini Kit (QIAGEN). RT-PCR is performed with 400 ng RNA each, using the TaqMan Gold RT-PCR Kit (Applied Biosystems). Primers are designed as follows: mouse TREM-1, forward 5'-GAGCTTGAAGGATGAGGAAGGC-3' and reverse 5'-CAGAGTCTGTCACTTGAAGGTCAGTC-3'; mouse TNF, forward 5'-GTAGCCCACGTCGTAGCAAA-3' and reverse 5'-ACGGCAGAGAGGAGGTTGAC-3'; mouse beta-actin, forward 5'-TGGAATCCTGTGGCATCCAT-GAAAC-3' and reverse 5'-TAAAACGCAGCTCAGTAA-CAGTCCG-3'; human TREM-1, forward 5'-CTTGGTGGT-GACCAAGGGTTTTTC-3' and reverse 5'-ACACCGGAACCCTGATGATATCTGTC-3'; human TNF, forward 5'-GCCCATGTTGTAGCAAACCC-3' and reverse 5'-TAGTCGGGCCGATTGATCTC-3'; human GAPDH, forward 5'-TTCACCACCATGGAGAAGGC-3' and reverse 5'-GGCATGGACTGTGGTCATGA-3'. PCR products are semiquantitatively analyzed on agarose gels.

Human TREM-1 and mouse TREM-1 and TNF expression is also assessed by real-time PCR using the TREM-1 QuantiTect primer assay system and QuantiTect SYBR green PCR Kit (both from QIAGEN). GAPDH is used to normalize TREM-1 and TNF expression levels. DNA is amplified on a 7500 Real-Time PCR system (Applied Biosystems), and the increase in gene expression is calculated using Sequence Detection System software (Applied Biosystems).

Western Blot Analysis

Protein samples are separated on a denaturing 12% acrylamide gel, followed by transfer to nitrocellulose filter and probing with the primary antibody. Anti-TREM-1 (polyclonal goat IgG, 0.1 ug/ml; R&D Systems) or anti-tubulin (clone B-5-1-2, 1:5,000; Sigma-Aldrich) is used as primary reagent. As secondary antibodies, HRP-labeled donkey anti-goat Ig (1:2,000; The Binding Site) and goat anti-mouse Ig (1:4,000; Sigma-Aldrich) are used. Binding is detected by chemiluminescence using a Super Signal West Pico Kit (Pierce).

Statistics

The unpaired 2-tailed Student t test is used to compare groups; P values less than 0.05 are considered significant.

Example 13

Modulation of the TREM-1 Pathway by Means of TREM-1 Peptide Variants During Severe Hemorrhagic Shock in Rats In order to demonstrate that the TREM-1 peptide variants are effective in inhibiting TREM-1-mediated cell activation and preventing organ dysfunction and improving survival in rats during severe hemorrhagic shock, the experiments can be conducted analogously to that described in Gibot et al. Shock 2009; 32:633-7, which is incorporated herein by reference in its entirety.

Materials and Methods

Animals

Adult male Wistar rats (250-300 g) are purchased from Charles River Laboratories (Wilmington, Mass., USA). After 1 week of acclimatization, rats are fasted 12 h before the experiments and are allowed free access to water. All the studies described in the succeeding sentences comply with the regulations concerning animal use and care published by the National Institutes of Health.

TREM-1 Peptide Variants

As described herein, TREM-1 peptide variants (e.g., the TREM-1 CP peptide, GFLSKSLVF) are chemically synthesized. A scrambled peptide containing the same amino acids but in a totally different sequence order (e.g., LFGFLVSSK) is similarly synthesized and serves as control peptide. Alternatively, a TREM-1 CP-A peptide (GFLSASLVF) is chemically synthesized and serves as control peptide.

Hemorrhagic Shock Model

Hemorrhagic shock is induced by bleeding from a heparinized (10 UI/mL) carotid artery catheter. Briefly, the rats are anesthetized (50 mg/kg pentobarbital sodium, i.p.) and kept on a temperature-controlled surgical board (37° C.). A tracheostomy is performed, and the animals are ventilated supine (tidal volume, 7-8 mL/kg; rodent ventilator no. 683; Harvard Apparatus, Holliston, Mass.) with a fraction of inspired oxygen of 0.3 and a respiratory rate of 60 breaths per minute. Anesthesia and respiratory support are maintained during the whole experiment. The left carotid artery and the left jugular vein are cannulated with PE-50 tubing. Arterial blood pressure is continuously monitored by a pressure transducer and an amplifier-recorder system (IOX EMKA Technologies, Paris, France). After a 30-min stabilization period, blood is drawn in 10 to 15 min via the carotid artery catheter until MAP reached 40 mmHg. Blood is kept at 37° C., and MAP is maintained between 35 and 40 mm Hg during 60 min. Rats are then allocated randomly (n=10-12 per group) to receive 0.1 mL of either saline (isotonic sodium chloride solution), TREM-1 peptide variant, or control peptide (various amounts of peptides in 0.1 mL of saline) solution over 1 min via the jugular vein (H0). Shed blood and ringer lactate (volume=3× shed volume) are then infused via the jugular vein in 60 min, and rats are observed for a 4-h period before being killed by pentobarbital sodium overdose. Killing occurs earlier if MAP decreased to less than 35 mm Hg.

Arterial Blood Gas, Lactate, and Cytokines

Arterial blood gas and lactate concentrations are determined hourly on an automatic blood gas analyzer (ABL 735; Radiometer, Copenhagen, Denmark). Concentrations of TNF-alpha and IL-6 and sTREM-1 in the plasma are determined in triplicate by enzyme-linked immunosorbent assay (Biosources, Nivelles, Belgium; RnD Systems, Lille, France).

Bacterial Translocation

Rats are killed under anesthesia, and mesenteric lymph node (MLN) complex, spleen, and blood are aseptically removed 4 h after the beginning of reperfusion (or earlier if MAP decreased<35 mm Hg). Homogenates of MLN and spleen and serial blood dilutions are plated and incubated overnight at 37° C. on Columbia blood agar plates (in carbon dioxide and anaerobically) and Macconkey agar (in air). Visible colonies are then counted.

Pulmonary Integrity

Additional groups of rats (n=4) are subjected to the same procedure but are also infused via the tail vein with fluorescein isothiocyanate (FITC)-albumin (5 mg/kg in 0.3 mL of phosphate-buffered saline) 2 h after the beginning of reperfusion. Rats in these groups are killed 2 h later with an overdose of sodium pentobarbital (200 mg/kg). Immediately thereafter, the lungs are lavaged three times with 1 mL of phosphate-buffered saline, and blood is collected by cardiac puncture. The bronchoalveolar lavage fluid (BALF) is pooled, and plasma is collected. Fluorescein isothiocyanate-albumin concentrations in BALF and plasma are determined fluorometrically (excitation, 494 nm; emission, 520 nm). The BALF-plasma fluorescence ratio is calculated and used as a measure of damage to pulmonary alveolar endothelial/epithelial integrity as previously described (Yang et al. Crit Care Med 2004; 32:1453-9).

Statistical Analysis

Data are analyzed using ANOVA or ANOVA for repeated measures when appropriate, followed by Newman-Keuls post hoc test. Survival curves are compared using the log-rank test. A two-tailed value of P less than 0.05 is deemed significant. All analyses are performed with GraphPad Prism software (GraphPad, San Diego, Calif.).

Example 14

Modulation of the TREM-1 Pathway by Means of TREM-1 Peptide Variants in a Mouse Model of Human Non-Small Cell Lung Cancer Tumorigenesis In order to demonstrate that the TREM-1 peptide variants are effective in inhibiting TREM-1-mediated cell activation and reducing tumor growth, tumor vascularity, and spontaneous metastases in animal models of human non-small cell lung cancer (NSCLC), the experiments can be conducted analogously to those disclosed in US Pat Appl 20080193375 and described elsewhere (Arenberg et al. J Clin Invest 1998; 102:465-72; Arenberg et al. J Clin Invest 1996; 97:2792-802; Arenberg et al. J Exp Med 1996; 184:981-92; Phillips et al. Am J Respir Crit Care Med 2003; 167:1676-86), which are incorporated herein by reference in its entirety.

Materials and Methods

TREM-1 Peptide Variants

As described herein, TREM-1 peptide variants (e.g., the TREM-1 CP peptide, GFLSKSLVF) are chemically synthesized. A scrambled peptide containing the same amino acids but in a totally different sequence order (e.g., LFGFLVSSK) is similarly synthesized and serves as control peptide. Alternatively, a TREM-1 CP-A peptide (GFLSASLVF) is chemically synthesized and serves as control peptide.

Human NSCLC-SCID Mouse Chimeras 4-6-wk-old female CB17-SCID mice (Taconic Farms, Germantown, N.Y.) with serum Ig<1 ug/ml are injected subcutaneously with human NSCLC cells ($1\times10^6$ cells in 100 ul) into each flank. The animals are maintained under sterile conditions in laminar flow rooms and killed in groups of six. At time of death, anticoagulated (heparin 50 U/500 ul of blood) blood is collected and centrifuged. The plasma is stored at $-70°$ C. for later analysis. Tumors are dissected from the mice and measured with a Thorpe caliper (Biomedical Research Instruments, Rockville, Md.). A portion of the tumor is fixed in 4% paraformaldehyde for histologic analysis and immunohistochemistry. H & E-stained sections are examined under 400× magnification to quantify infiltrating neutrophils. 10 fields are examined in each of nine tumor sections from both TREM-1 peptide variant- and control peptide-treated groups. Results are expressed as the number of cells per high power field (HPF; 400×). The other portion of the tumor is snap frozen for subsequent homogenization and sonication in antiprotease buffer followed by filtration through 0.45-um filters (Acrodiscs, Gelman Sciences, Ann Arbor, Mich.). The filtrate is stored at 70° C. for later analysis. All tumor homogenates are standardized for total protein prior to lyophilization (SpeedVac, Savant) and used in the corneal micropocket model of neovascularization. The right lung is inflated with 4% paraformaldehyde, and prepared for histopathologic analysis, or processed for FACS analysis (CD49b) of human cell populations (A549 cells). In the TREM-1 inhibition studies, SCID mice receive intraperitoneal (i.p.) injections of 500 ul of either TREM-1 peptide variant, or control peptide, or no treatment, every 48 h for 6 wk, starting at the time of cell inoculation. Tumor specimens from these mice are processed as described above.

Corneal micropocket model of angiogenesis.

In vivo angiogenic activity of the tumors is assayed in the avascular cornea of Long Evans rat eyes, as previously described (Koch et al. Arthritis Rheum 1989; 29:471-9). Briefly, equal volumes of lyophilized tumor specimens normalized to total protein, are combined with sterile Hydron (Interferon Sciences Inc.) casting solution. 5-ul aliquots are pipetted onto the flat surface of an inverted sterile polypropylene specimen container, and polymerized overnight in a laminar flow hood under UV light. Prior to implantation, pellets are rehydrated with normal saline. Animals are given i.p. ketamine (150 mg/kg) and atropine (250 ug/kg) for anesthesia. Rat corneas are anesthetized with 0.5% proparacaine hydrochloride ophthalmic solution followed by implantation of the Hydron pellet into an intracorneal pocket (1-2 mm from the limbus). 6 d after implantation, animals receive heparin (1000 U) of and ketamine (150 mg/Kg) i.p., followed by a 10 ml perfusion of colloidal carbon via the left ventricle. Corneas are harvested and photographed. Positive neovascularization responses were defined as sustained directional in growth of capillary sprouts and hairpin loops towards the implant are observed. Negative responses are defined as either no growth or only an occasional sprout or hairpin loop displaying no evidence of sustained growth.

Quantitation of Vessel Density

Quantitation of vessel density is performed using a modification of the previously described method (Weidner N. Am J Pathol 1995; 147:9-19). Briefly, tissue sections are dewaxed with xylene and rehydrated through graded concentrations of ethanol. Slides are blocked with normal rabbit serum (BioGenex, San Ramon, Calif.), and overlaid with 1:500 dilution of either control (goat) or goat anti-Factor VIII-related antigen antibodies. Slides are then rinsed and overlaid with secondary biotinylated rabbit anti-goat IgG (1:35) and incubated for 60 min. After washing twice with Tris-buffered saline, slides are overlaid with a 1:35 dilution of alkaline phosphatase conjugated to streptavidin (BioGenex), and incubated for 60 min. Fast Red (BioGenex) reagent was used for chromogenic localization of Factor VIII antigen. After optimal color development, sections are immersed in sterile water, counterstained with Mayer's hematoxylin, and cover slipped using an aqueous mounting solution. A549 tumor specimens from TREM-1 peptide variant- and control peptide-treated SCID mice are examined in a blinded fashion for the presence of Factor VIII immunolocalization. Sections are first scanned at low magnification (40×) to identify vascular "hot spots." Areas of greatest vessel density are then examined under higher magnification (400×) and counted. Any distinct area of positive staining for Factor VIII is counted as a single vessel. Results are expressed as the mean number of vessels±SEM per high power field (HPF; 400×). A total of 30 HPFs are examined and counted from three tumors of each of the treatment groups.

FACS analysis for human CD49b (A549 lung metastases). Before removal, lungs from human NSCLC tumor bearing animals are perfused with normal saline, and dissected free of the thoracic cavity. The right lung is minced, and incubated for 1 h in digestion media (RPMI with 0.02% collagenase type IV, and 0.1 mg of bovine pancreas grade II DNaseI). Cells are further separated by repeatedly aspirating the cell suspension through a 20-ml syringe. Cells are then pelleted at 600 g for 10 min, resuspended in sterile water for 30 s to lyse remaining RBCs, washed in 1×PBS, and resuspended in complete media with 5% FCS. Cells are counted, transferred at a concentration of $5×10^6$ cells/ml to fluorescent antibody buffer (1% FA buffer [Difco No. 2314-15], 1% FCS, and 0.1% azide), and maintained at 4° C. for the remainder of the staining procedure. 100 ul of cells are labeled with FITC-conjugated rat anti-human CD49b (1 ug, Pharmingen, San Diego, Calif.). This antibody recognizes the alpha-2 portion of the beta-1-integrin, VLA-2, a marker previously found to be expressed by A549 and Calu 1 cells. FITC-conjugated rat IgG is used as a control antibody. Unbound antibody is washed with FA buffer and the cell suspension is analyzed with FACS (Becton Dickinson). The data are expressed as the percentage of cells staining positively with anti-human CD49b.

Statistical Analysis

The studies involve a minimum of six human NSCLC/SCID mouse chimeras at each time point or for each manipulation. Groups of data are evaluated by analysis of variance to indicate groups with significant differences. Data that appear statistically significant are compared by Student's t test for comparing the means of multiple groups, and are considered significant if p values are less than 0.05. Results were presented as means±SEM. Data are analyzed using Statview II statistical software package (Abacus Concepts, Inc.).

INCORPORATION BY REFERENCE

All of the patents and publications cited herein are hereby incorporated by reference. Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

The references cited herein throughout, to the extent that they provide exemplary procedural or other details supplementary to those set forth herein, are all specifically incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A peptide comprising an amino acid sequence consisting of R1-AA1-AA2-A1-A2-B1-B2-C1-D1-E1-F1-G1-G2-H1-H2-HH1-HH2-R2, wherein:
    R1 is absent or is selected from the group consisting of N-terminal sugar conjugate and N-terminal lipid conjugate;
    AA1 is absent or is selected from the group consisting of Arg, Arg-Arg, Arg-Arg-Arg and Arg-Arg-Arg-Arg;
    AA2 is absent or is selected from the group consisting of Lys, Lys-Lys, Lys-Lys-Lys and Lys-Lys-Lys-Lys;
    A1 is absent or is selected from the group consisting of Ser, Thr, Pro, Phe, Leu, Ala, Val, Ile, Met, Trp, a two amino acide peptide, a three amino acide peptide, a four amino acide peptide, a five amino acide peptide and a six amino acid peptide, said peptide consisting of Ser, Thr, Pro, Phe, Leu, Ala, Val, Ile, Met and Trp in any combination;
    A2 is absent or is a positively charged amino acid selected from the group comprising Arg, Lys and His;
    B1 is selected from the group consisting of Gln, Ser, Gly, Tyr, Cys, Thr, Asn and a two amino acid peptide, said peptide consisting of Gln, Ser, Gly, Tyr, Cys, Thr and Asn in any combination;
    B2 is absent or is a positively charged amino acid selected from the group comprising Arg, Lys and His;
    C1 is selected from the group consisting of Pro, Phe, Leu, Ala, Val, Ile, Met, Trp and a two amino acid peptide, said peptide consisting of Pro, Phe, Leu, Ala, Val, Ile, Met and Trp in any combination;
    D1 is selected from the group consisting of Gln, Ser, Gly, Tyr, Cys, Thr and Asn;
    E1 is a positively charged amino acid selected from the group comprising Arg, Lys and His;
    F1 is selected from the group consisting of Gln, Ser, Gly, Tyr, Cys, Thr and Asn;
    G1 is selected from the group consisting of Pro, Phe, Leu, Ala, Val, Ile, Met, Trp, a two amino acide peptide and a three amino acide peptide, said peptide consisting of Pro, Phe, Leu, Ala, Val, Ile, Met and Trp in any combination;
    G2 is absent or is a positively charged amino acid selected from the group comprising Arg, Lys and His;
    H1 is absent or is selected from the group consisting of Ser, Thr, Pro, Phe, Leu, Ala, Val, Ile, Met, Trp, a two amino acide peptide, a three amino acide peptide, a four amino acide peptide, a five amino acide peptide and a six amino acid peptide, said peptide consisting of Ser, Thr, Pro, Phe, Leu, Ala, Val, Ile, Met and Trp in any combination;
    H2 is absent or is a positively charged amino acid selected from the group comprising Arg, Lys and His;
    HH1 is absent or is selected from the group consisting of Arg, Arg-Arg, Arg-Arg-Arg and Arg-Arg-Arg-Arg;
    HH2 is absent or is selected from the group consisting of Lys, Lys-Lys, Lys-Lys-Lys and Lys-Lys-Lys-Lys; and
    R2 is absent or is C-terminal lipid conjugate.

2. The peptide of claim 1, wherein the distance between A2 and E1 is six amino acid residues.

3. The peptide of claim 1, wherein the distance between B2 and E1 is three amino acid residues.

4. The peptide of claim 1, wherein the distance between E1 and G2 is three amino acid residues.

5. The peptide of claim 1, wherein the distance between E1 and H2 is six amino acid residues.

6. The peptide of claim 1, wherein the distance between A2 and E1 is six amino acid residues, the distance between B2 and E1 is three amino acid residues, the distance between E1 and G2 is three amino acid residues and the distance between E1 and H2 is six amino acid residues.

7. The peptide of claim 1, wherein said N-terminal sugar conjugate is 1-amino-glucose succinate.

8. The peptide of claim 1, wherein said N-terminal lipid conjugate is selected from the group comprising 2-aminododecanoate and myristoylate conjugates.

9. The peptide of claim 1, wherein said C-terminal lipid conjugate is selected from the group comprising Gly-Tris-monopalmitate, Gly-Tris-dipalmitate and Gly-Tris-tripalmitate conjugates.

10. The peptide of claim 1, wherein the peptide is attached to a carrier molecule.

11. The peptide of claim 1, wherein the peptide is conjugated at a free amine group with a polyalkylene glycol.

12. The peptide of claim 11, wherein the polyalkylene glycol is polyethylene glycol.

13. The peptide of claim 1, wherein one or more amino acid is a D-amino acid.

14. The peptide of claim 1, wherein said amino acid sequence further comprises at least one amino acid selected from the group consisting of an L-amino acid and a D-amino acid.

15. The peptide of claim 1, wherein said peptide is a cyclic peptide.

16. The peptide of claim 1, wherein said peptide is a cyclic dimer peptide.

17. The peptide of claim 1, wherein said peptide is a dimer peptide.

18. A method of treating a subject suffering from a disease or condition in which myeloid cells are involved or recruited, said method comprising administering to the subject a therapeutically effective amount of the peptide of claim 1 so as to treat a disease or condition in said subject.

19. A method comprising:
   a) providing; i) a patient having at least one symptom of a disease or condition in which myeloid cells are involved or recruited; and ii) the peptide of claim 1;
   b) administering said peptide to said patient under conditions such that said at least one symptom is reduced.

20. The method of claim 19, wherein the disease or condition is a sepsis.

21. The method of claim 19, wherein the disease or condition is a lung cancer.

22. The method of claim 19, wherein the disease or condition is an inflammatory bowel disease.

23. The method of claim 19, wherein the disease or condition is an acute mesenteric ischemia.

24. The method of claim 19, wherein the disease or condition is a hemorrhagic shock.

25. The method of claim 19, wherein the disease or condition is a rheumatic disease.

26. The method of claim 25, wherein the rheumatic disease is selected from the group consisting of arthritis, ankylosing spondylitis, fibromyalgia, lupus, scleroderma, polymyositis, dermatomyositis, polymyalgia rheumatica, bursitis, tendinitis, vasculitis, carpal tunnel syndrome, complex regional pain syndrome, juvenile arthritis, Lyme disease, systemic lupus erythematosus, Kawasaki disease, fibromyalgia, and chronic fatigue syndrome.

27. The method of claim 19, wherein the disease or condition is a myeloid cell-related inflammatory condition.

28. The method of claim 27, wherein the myeloid cell-related inflammatory conditions is selected from the group comprising myositis and tissue and organ rejection.

* * * * *